United States Patent [19]

Wolfe et al.

[11] Patent Number: 5,552,543
[45] Date of Patent: Sep. 3, 1996

[54] SIX-MEMBERED HETERO "N" COMPOUNDS

[75] Inventors: Saul Wolfe, Kingston; Stephen Bruder, Glenburnie, both of Canada

[73] Assignee: Simon Fraser University, Vancouver, Canada

[21] Appl. No.: 219,803

[22] Filed: Nov. 4, 1993

Related U.S. Application Data

[63] Continuation of Ser. No. 892,716, May 29, 1992, which is a continuation of Ser. No. 450,988, Dec. 15, 1989, which is a continuation-in-part of Ser. No. 284,502, Dec. 14, 1988, abandoned.

[51] Int. Cl.[6] ............................................. C07D 279/12
[52] U.S. Cl. ........................ 544/58.4; 544/58.1; 544/106; 544/162; 544/172; 546/245
[58] Field of Search ............................... 540/215, 222, 540/225; 546/245; 544/58.4, 58.1, 106, 162, 172

[56] References Cited

U.S. PATENT DOCUMENTS 4,499,265  2/1985  Torii et al. ............................ 540/215

FOREIGN PATENT DOCUMENTS 891477  9/1958  United Kingdom .

OTHER PUBLICATIONS

Chemical Abstracts vol. 121: 157589(1994).
Chemical Abstracts vol. 114: 101534(1991).
Chemical Abstracts vol. 75: 110156(1971).
Kelly et al. *J. Biol Chem* 1985 vol. 260(10), pp. 6449–6458.
Wolfe et al. *Can J. Chem.* 1988 vol. 66(11) pp. 2733–2750.

*Primary Examiner*—Nicholas Rizzo
*Attorney, Agent, or Firm*—Oyen Wiggs Green & Mutala

[57] ABSTRACT

Novel six-membered hetero "N" compounds having antibiotic activity, represented by the formula:

where
$X = S, O, CH_2,$ or $Se$
$Y = OH, NH_2, NHCOR_9,$ or $SH$
$R_1, R_2, R_3, R_4, R_5, R_6, R_7$ (which may be identical or different) $= H$, alkyl, or aryl
$R_9 = $ a β-lactam active side chain;
computer models for evaluating such compounds and processes for preparing them.

14 Claims, No Drawings

SIX-MEMBERED HETERO "N" COMPOUNDS

CROSS REFERENCE TO RELATED APPLICATION

This application is a continuation of application Ser. No. 07/892,716 filed May 29, 1992, abandoned which in turn is a continuation of application Ser. No. 07/450,988 abandoned filed Dec. 15, 1989, which is a continuation-in-part of prior application Ser. No. 284,502 filed 14 Dec. 1988, abandoned.

FIELD OF INVENTION

This invention relates to novel antibacterial agents and a method for predicting the activity thereof relative to penicillin. More particularly, this application describes a molecular modelling technique for determining the fit and reactivity of candidate compounds with bacterial cell wall receptors, and hence a method for predicting structural types that exhibit activity.

BACKGROUND OF INVENTION

It has been known since the 1940's that β-lactam antibiotics, such as the penicillins and cephalosporins, are effective by reason of their interference with the integrity of bacterial cell walls. It has also been discovered that the interference is effected by covalent bonding to the active site serine residue of one or more of a group of enzymes termed penicillin binding proteins (PBP's). These enzymes serve to complete bacterial cell wall synthesis by a cross linking of peptidoglycan chains, and are essential to the cells. All known PBP's include a sequence -Ser-X-X-Lys- and the simplest kinetic description of the reaction between a PBP and a β-lactam antibiotic is given in equation 1, below, where A is a generalized structure. Since the PBP is regenerated in the deacylation step, useful antibacterial activity is considered to require $k_3/K \geq 1000 M^{-1} sec^{-1}$ and $k_4 \leq 1 \times 10^{-4} sec^{-1}$.

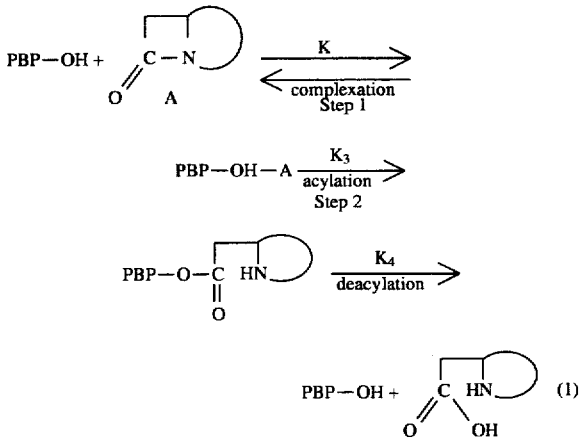

The question is, therefore, what is the correlation, if any, between antibacterial activity and the "lock and key" interactions which take place between the PBP and the antibiotic.

OBJECT OF THE INVENTION

It is, therefore, an object of the present invention to determine the correlation between antibacterial activity and the lock and key interactions between PBP's and selected antibiotics and thus provide a means by which the "fit" (Step 1) and "reactivity" (Step 2) of any selected candidate structure relative to the fit and reactivity of penicillin may be predicted with some degree of quantitative accuracy.

It is another object of this invention to design with this model novel non β-lactam compounds having antibacterial activity.

BRIEF STATEMENT OF INVENTION

Thus by one aspect of this invention there is provided a method for determining fit and reactivity of any selected candidate antibacterial compound comprising (a) simulating the reaction of said compound with a model of a penicillin binding protein which includes a serine-lysine active site, by determining the relative ease of formation of a four-centred relationship between OH of said serine and a reactive site of said compound; and (b) determining the activation energy for the four-centred reaction of the chemically active functional group of said compound with methanol relative to the activation energy of the corresponding reaction of methanol with N-methylazetidinone.

By another aspect of this invention there is provided a example of a non-β-lactam containing compound characterized in that said compound is capable of forming a four-centred transition structure which includes a serine OH group contained in a model of a penicillin binding protein, reacted therewith; said compound having an activation energy for reaction with methanol not greater than 3 kcal/mol higher than the activation energy exhibited by N-methylazetidinone.

Another aspect of this invention provides compounds of the formula:

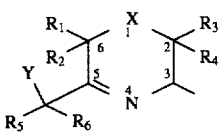

where

X=S, O, $CH_2$, NH, $NR_7$, Se

Y=OH, $NH_2$, $NHCOR_8$, SH $R_1, R_2, R_3, R_4, R_5, R_6, R_7$-alkyl, aryl $R_8$ is a β-lactam active side chain, and pharmaceutically acceptable salts thereof.

β-lactam active side chains are side chains known to be active in β-lactam antibiotics. As used herein, the substituents acceptable in beta-lactam antibiotics may be any of the wide range of permissible substituents disclosed in the literature pertaining to penicillin and cephalosporin compounds. Such substituents may, for example, comprise a group of the formula

—XQ wherein X represents oxygen or sulfur and Q represents $C_{1-4}$ alkyl (e.g., methyl or ethyl), $C_{2-4}$ alkenyl (e.g. vinyl or propenyl) or aryl $C_{1-4}$ alkyl (e.g., phenyl $C_{1-4}$ alkyl such as benzyl).

Such substituents also may be, for example, an unsaturated organic group, for example, a group of the formula

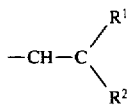

Wherein $R_1$ and $R_2$ which may be the same or different, and are each selected from hyudrogen, carboxy, cyano, $C_{2-7}$ alkoxycarbonyl (e.g., methoxycarbonyl or ethoxycarbonyl), and substituted or unsubstituted aliphatic (e.g., alkyl, preferably $C_1-C_6$ alkyl such as methyl, ethyl, isopropyl or no-propyl). Specific substituted vinyl groups of the above formula include 2-carboxyvinyl, 2-methoxycarbonylvinyl, 2-ethoxycarbonylvinyl and 2-cyanovinyl.

Alternatively, the β-lactam acceptable substituent may also be an unsubstituted or substituted methyl group depicted by the formula

wherein Y is a hydrogen atom or a nucleophilic atom or group, e.g., the residue of a nucleophile or a derivitive of a residue of a nucleophile. Y may thus, for example, be derived from the wide range of nucleophilic substances characterized by possessing a nucleophilic nitrogen, carbon, sulfur or oxygen atom. Such nucleophiles have been widely described in the patent and technical literature respecting β-lactam chemistry and are exemplified, for example, in Foxton et al U.S. Pat. No. 4,385,177 granted May 24, 1983, at column 4, line 42—column 8, line 24 and column 34, line 51—column 36, line 17, the disclosure of which is incorporated by this reference herein.

Yet another aspect of this invention provides compounds of the formula:

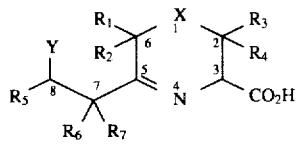

where
X=S, O, $CH_2$, NH, $NR_8$, Se
Y=OH, $NH_2$, $NHCOR_9$, SH
$R_1$, $R_2$, $R_3$, $R_4$, $R_5$, $R_6$, $R_7$, $R_8$-alkyl, aryl
$R_9$ is a list of 30–40 side chains known to be active in β-lactam antibiotics, and pharmaceutically acceptable salts thereof A further aspect of this invention provides compounds of the formula:

where
X—Y=S—S, $CH_2CH_2$, S—$CH_2$, $CH_2$—S, S—$NR_8$, $NR_8$—S, $CH_2H$—O, O—$CH_2$, O—$NR_8$, $NR_9$—O, Se—Se, $CH_2$—$CH_2$, Se—$CH_2$  Z=OH, $NH_2$, $NHCOR_9$, SH
$R_1$, $R_2$, $R_3$, $R_4$, $R_5$, $R_6$, $R_8$-alkyl, aryl $R_7$=alkyl, aryl
$R_9$ is a list of 30–40 side chains known to be active in β-lactam antibiotics, and pharmaceutically acceptable salts thereof.

A still further aspect of the invention provides compounds of the formula:

where
X=S, O, $CH_2$, NH, $NR_6$, Se
Y=N, CH, $CR_7$
Z=OH, $NH_2$, SH, $NHCOR_8$ (when Y=N)
Z—$R_9$ (when Y=CH, $CR_7$)
$R_1$=$R_2$=$R_3$=$R_4$=$R_6$=$R_7$=alkyl, aryl
$R_5$=H, alkyl, aryl
$R_8$ is a list of 30–40 side chains known to be active in β-lactam antibiotics $R_9 = R_{10}$—CH—
       |
       $R_{11}$ where $R_{10}$=alkyl, aryl, and
$R_{11}$ =OH, $NH_2$, $NHCOR_8$ SH
and pharmaceutically acceptable salts thereof.

Another aspect of the invention provides compounds of the formula:

where
X=S, O, $CH_2$, NH, $NR_5$, Se
Y=$NR_6$—Z
$R_1$, $R_2$, $R_3$, $R_4$, $R_5$, and $R_6$ are each H, alkyl, or aryl Z is OH, SH, $NH_2$, or $NHCOR_7$
$R_7$ is a β-lactam active side chain, and pharmaceutically acceptable salts thereof. Preferably, $R_6$ is hydrogen and Z is $NHCOR_9$ where $R_9$ is lower alkyl and particularly benzyl.

As used herein, the term "alkyl" includes alkyl groups containing up to twenty carbon atoms, preferably $C_{1-6}$ alkyl groups, which can optionally be monosubstituted, distributed or polysubstituted by functional groups, for example by free, etherified is esterified hydroxyl or mercapto groups, such as lower alkoxy or lower alkylthio; optionally substituted lower alkoxycarbonyloxy or lower alkanoyloxy; halogen; oxo; nitro; optionally substituted amino, for example lower alkylamino, di-lower alkylamino, lower alkanoyloxy; halogen; oxo; nitro; optionally substituted amino, for example lower alkylamino, di-lower alkylamino, lower alkyleneamino, as well as acylamino, such as lower alkanoylamino, lower alkoxycarbonylamino, halogeno-lower alkoxycarbonylamino, optionally substituted carbamoylamino, ureidocarbonylamino or guanidinocarbonylamino, and also sulfoamino which is optionally present in the form of a salt, such as in the form of an alkali metal salt, azido, or acyl, such as lower alkanoyl or benzoyl;

Optionally functionally modified carboxyl, such as carboxyl present in the form of a salt, esterfied carboxyl, such as lower alkoxycarbonyl, optionally substituted carbamoyl, such as N-lower alkylcarbamoyl or N, N-di-lower alkylcarbamoyl and also optionally substituted ureidocarbonyl or guanidinocarbonyl; nitrile; optionally functionally modified sufo, such as sulfamoyl or sulfo present in the form of a salt; or optionally O-monosubstituted or O, O-disubstituted phosphone, which may be substituted, for example, by optionally substituted lower alkyl, phenyl or phenyl-lower alkyl, it also being possible for O-unsubstituted or O-monosubstituted phosphono to be in the form of a salt, such as in the form of an alkali metal salt.

As used herein, the term "aryl" includes carbocyclic, hetrocyclic aryl. The carbocyclic aryl includes phenyl and naphthyl, optionally substituted with up to three halogen, $C_{1-6}$ alkyl, $C_{1-6}$ alkoxy, halo $(C_{1-6})$ alkyl, hydroxy, amino, carboxy, $C_{1-6}$ alkoxycarbonyl, $C_{1-6}$ alkoxycarbonyl-$(C_{1-6})$-alkyl, nitro, sulfonamido, $C_{1-6}$ alkylcarbonyl, amido (—$CONH_2$), or $C_{1-6}$ alkylamino groups.

The term "heterocyclic" includes single or fused rings comprising up to four hetro atoms in the ring selected from oxygen, nitrogen and sulphur and optionally substituted with up to three halogen $C_{3-6}$ alkyl, $C_{1-6}$ alkoxy, halo $(C_{1-6})$ alkyl, hydroxy, amino, carboxy, $C_{1-6}$ alkoxycarbonyl, $C_{1-6}$ alkoxycarbonyl $(C_{1-6})$ alkyl, aryl, oxo, nitro, sulphonamido, $C_{1-6}$ alkyl-carbonyl, amido or $C_{1-6}$ alkylamino groups.

Suitable $C_{1-6}$ alkyl groups may be straight or branched chain and include methyl, ethyl n- or iso-propyl, n-, sec-, iso-, or tert-butyl. In those cases where the $C_{1-6}$ alkyl group carries a substituent the preferred $C_{1-6}$ alkyl groups include methyl, ethyl and n-propyl.

BRIEF DESCRIPTION OF DRAWINGS

FIG. 1 is the structure of a model of a penicillin receptor whose docking to penicillins and cephalosporins leads uniformly to four-centred interactions between C—O—H of serine and (O)C—N of the penicillin or cephalosporin.

FIG. 2 is a stereoscopic view of penicillin V docked to the peptide of FIG. 1.

FIG. 3 is a stereoscopic view of a $\Delta^3$-cephalosporin docked to the peptide of FIG. 1.

FIG. 4 is a stereoscopic view of a $\Delta^2$-cephalosporin docked to the peptide of FIG. 1.

FIG. 5 is a stereoscopic view of a 4-epi-$\Delta^2$-cephalosporin docked to the peptide of FIG. 1.

FIG. 6 is a close-up view of the four-centred interaction between C—O—H of serine and (O)C—N of the β-lactam ring which exists in FIG. 2.

FIG. 7 is the N-protonated transition structure for the attack of methanol upon the exo face of N-methylazetidinone (ab initio calculation).

FIG. 8 is the O-protonated transition structure for the attack of methanol upon the exo face of N-methylazetidinone (ab initio calculation).

FIG. 9 is a stereoscopic view of the transition structure calculated using MINDO/3 for the reaction of methanol with a penicillin via an N-protonated pathway.

FIG. 10 is a stereoscopic view of the transition structure calculated using MINDO/3 for the reaction of methanol with a penicillin via an O-protonated pathway.

FIG. 11 is a stereoscopic view of the transition structure for the reaction of methanol with penam via endo-attack.

FIG. 12 is a stereoscopic view of the complexation of 5 to the peptide of FIG. 1.

DETAILED DESCRIPTION OF PREFERRED EMBODIMENTS

Possible structures for peptides, penicillins and cephalosporins were examined using the computer programme MMP2(85) which is available from the Quantum Chemistry Program Exchange (QCPE) at the University of Indiana, Bloomington, Ind., U.S.A. This programme calculates the strain energy of a molecule in terms of contributions to this energy associated with stretching of bonds, bending of bond angles, torsion about bonds, and electrostatic and van der Waals interactions of non-bonded atoms. To carry out the calculation, it is necessary to enter the cartesian coordinates of all atoms, and define lists of connected and attached atoms. If the types of atoms present in the molecule of interest are known to the programme, the strain energy is minimized by application of the Newton-Raphson procedure to an unconstrained multivariable non-linear function that includes all of the individual contributions noted above. This function is termed the force field. For the minimization to proceed in a reliable manner it is important that the geometry entered at the beginning of the calculation already be reasonably accurate, and close to the bottom of an energy well.

For each different molecule to be examined with MMP2(85), it is first necessary to determine the parameters associated with the types of atoms present within this molecule. These parameters include, inter alia, standard bond lengths and bond angles, and stretching and bending force constants. Bond lengths and angles are available from compilations of vibrational data, and others can be calculated by molecular orbital (MO) procedures. The general strategy for parameter development can be found in the monograph "Molecular Mechanics", by U. Burkert and N. L. Alinger, published by the American Chemical Society, Washington, 1982. Since the parameters for peptides (e.g., enzymes), penicillins and cephalosporins in the force field of MMP2(85) were previously unknown, these were first determined and tested for their ability to reproduce known experimental crystal structures, and known effects of solvent upon the conformations (three-dimensional structures) of the different structural types. The parameters are termed PEPCON (Table 1) (for peptides), PENCON (Table 2) (for penicillins), and CEPARAM (Table 3) (for cephalosporins).

TABLE 1

| PEPCON | | | | | | |
|---|---|---|---|---|---|---|
| 159 | 39 | 9 | 123 | 39 | | 78.50 |
| 5 | 6 | 1 | 5 | 0.00 | 0.00 | 0.30 |
| 5 | 3 | 9 | 1 | 0.00 | 15.00 | 0.00 |
| 3 | 9 | 1 | 6 | 0.00 | 0.00 | 0.00 |
| 9 | 1 | 6 | 5 | −2.50 | 3.00 | −1.00 |
| 6 | 1 | 9 | 14 | 0.00 | 0.00 | 0.00 |
| 1 | 1 | 1 | 1 | 0.20 | 0.27 | 0.09 |
| 1 | 1 | 1 | 3 | 0.26 | 0.00 | 0.06 |
| 1 | 1 | 1 | 5 | 0.00 | 0.00 | 0.27 |
| 1 | 1 | 1 | 8 | 0.00 | 0.00 | 0.06 |
| 1 | 1 | 1 | 9 | 0.00 | 0.00 | 0.06 |
| 1 | 1 | 1 | 13 | 0.00 | 0.00 | 0.40 |
| 1 | 1 | 1 | 15 | 0.00 | 0.00 | 0.80 |
| 1 | 1 | 1 | 19 | 0.00 | 0.00 | 0.60 |
| 1 | 1 | 2 | 2 | 0.00 | 0.00 | 0.10 |
| 1 | 1 | 3 | 7 | 0.00 | 0.00 | −0.04 |
| 1 | 1 | 3 | 9 | 0.00 | 0.00 | −0.04 |
| 1 | 1 | 3 | 11 | 0.00 | 0.00 | −0.09 |
| 1 | 1 | 3 | 12 | 0.00 | 0.00 | −0.20 |
| 1 | 1 | 4 | 4 | 0.00 | 0.00 | 0.10 |
| 1 | 1 | 4 | 26 | 0.00 | 0.00 | 0.10 |
| 1 | 1 | 4 | 27 | 0.00 | 0.00 | 0.10 |

TABLE 1-continued

PEPCON

| | | | | | | |
|---|---|---|---|---|---|---|
| 1 | 1 | 6 | 21 | 0.00 | 0.00 | 0.30 |
| 1 | 1 | 8 | 23 | 0.00 | 0.00 | 0.30 |
| 1 | 1 | 9 | 1 | 0.00 | 0.00 | 0.12 |
| 1 | 1 | 9 | 3 | 0.00 | 0.00 | 0.06 |
| 1 | 1 | 9 | 14 | 0.00 | 0.00 | 0.06 |
| 1 | 1 | 13 | 23 | 0.00 | 0.00 | 0.20 |
| 1 | 1 | 15 | 1 | 0.00 | 0.00 | 0.70 |
| 1 | 1 | 15 | 15 | 0.00 | 0.00 | 0.80 |
| 1 | 1 | 15 | 25 | 0.00 | 0.00 | 0.20 |
| 1 | 1 | 19 | 2 | 0.00 | 0.00 | 0.05 |
| 1 | 1 | 19 | 23 | 0.00 | 0.00 | 0.05 |
| 1 | 2 | 2 | 2 | 0.00 | 3.50 | 0.00 |
| 1 | 2 | 2 | 5 | 0.00 | 3.50 | 0.00 |
| 1 | 3 | 9 | 1 | 1.80 | 6.49 | 0.00 |
| 1 | 3 | 9 | 1 | 1.80 | 19.00 | 0.00 |
| 1 | 3 | 9 | 14 | 0.00 | 2.66 | 0.00 |
| 1 | 3 | 12 | 24 | 0.60 | 0.00 | 3.20 |
| 1 | 4 | 4 | 5 | −0.30 | 3.80 | 0.00 |
| 1 | 4 | 4 | 26 | 0.00 | 3.50 | 0.00 |
| 1 | 4 | 26 | 4 | 0.00 | 5.00 | 0.00 |
| 1 | 4 | 26 | 23 | 0.00 | 5.00 | 0.00 |
| 1 | 4 | 27 | 2 | −0.30 | 3.80 | 0.00 |
| 1 | 4 | 27 | 27 | 0.00 | 3.50 | 0.00 |
| 1 | 9 | 1 | 3 | 0.00 | 0.00 | 0.12 |
| 1 | 9 | 1 | 5 | 0.00 | 0.00 | 0.12 |
| 1 | 9 | 3 | 7 | 0.00 | 7.19 | 0.00 |
| 1 | 15 | 1 | 5 | 0.00 | 0.00 | 0.70 |
| 1 | 15 | 15 | 1 | 0.00 | −7.60 | 1.70 |
| 1 | 19 | 2 | 8 | 0.00 | 4.50 | 0.00 * |
| 1 | 19 | 2 | 19 | 0.00 | 4.50 | 0.00 |
| 2 | 1 | 1 | 3 | 0.26 | 0.00 | 0.06 |
| 2 | 1 | 1 | 5 | 0.00 | 0.00 | 0.27 |
| 2 | 1 | 1 | 8 | 0.00 | 0.00 | 0.06 |
| 2 | 1 | 1 | 9 | 0.00 | 0.00 | 0.06 |
| 2 | 1 | 1 | 13 | 0.00 | 0.00 | 0.06 |
| 2 | 1 | 3 | 7 | 0.00 | 0.00 | −0.35 |
| 2 | 1 | 3 | 9 | 0.00 | −0.50 | −1.70 |
| 2 | 2 | 1 | 3 | 0.00 | 0.00 | 0.90 |
| 2 | 2 | 1 | 5 | 0.00 | 0.00 | 0.05 |
| 2 | 2 | 2 | 2 | −0.30 | 3.80 | 0.00 |
| 2 | 2 | 2 | 5 | 0.00 | 3.50 | 0.00 |
| 2 | 2 | 2 | 6 | 0.00 | 3.80 | 0.00 |
| 2 | 2 | 2 | 27 | −0.30 | 3.80 | 0.00 |
| 2 | 2 | 6 | 21 | 0.00 | 1.80 | 0.00 |
| 2 | 2 | 27 | 4 | 0.00 | 3.50 | 0.00 |
| 2 | 2 | 27 | 26 | 0.00 | 3.50 | 0.00 |
| 2 | 2 | 27 | 27 | −0.30 | 3.80 | 0.00 |
| 2 | 19 | 1 | 5 | 0.00 | 0.00 | 0.05 |
| 2 | 27 | 4 | 4 | 0.00 | 3.50 | 0.00 |
| 2 | 27 | 26 | 4 | 0.00 | 5.00 | 0.00 |
| 2 | 27 | 26 | 23 | 0.00 | 5.00 | 0.00 |
| 2 | 27 | 27 | 2 | −0.30 | 3.80 | 0.00 |
| 2 | 27 | 27 | 4 | 0.00 | 3.50 | 0.00 |
| 2 | 27 | 27 | 26 | 0.00 | 3.50 | 0.00 |
| 3 | 1 | 1 | 3 | 0.26 | 0.00 | 0.06 |
| 3 | 1 | 1 | 4 | 0.26 | 0.00 | 0.06 |
| 3 | 1 | 1 | 5 | 0.00 | 0.00 | 0.16 |
| 3 | 1 | 1 | 6 | 0.26 | 0.00 | 0.06 |
| 3 | 1 | 1 | 8 | 0.00 | 0.00 | 0.06 |
| 3 | 1 | 1 | 9 | 0.00 | 0.00 | 0.08 |
| 3 | 1 | 1 | 13 | 0.00 | 0.00 | 0.06 |
| 3 | 1 | 1 | 15 | 0.26 | 0.00 | 0.06 |
| 3 | 1 | 8 | 23 | 0.00 | 0.00 | 0.30 |
| 3 | 1 | 9 | 3 | 0.00 | 0.00 | 0.06 |
| 3 | 1 | 9 | 14 | 0.00 | 0.00 | 0.06 |
| 3 | 1 | 13 | 23 | 0.00 | 0.00 | 0.30 |
| 3 | 9 | 1 | 5 | 0.00 | 0.00 | 0.06 |
| 4 | 1 | 1 | 5 | 0.00 | 0.00 | 0.27 |
| 4 | 1 | 1 | 8 | 0.00 | 0.00 | 0.06 |
| 4 | 1 | 1 | 9 | 0.00 | 0.00 | 0.06 |
| 4 | 1 | 1 | 13 | 0.00 | 0.00 | 0.06 |
| 4 | 4 | 1 | 5 | 0.00 | 0.00 | 0.10 |
| 4 | 4 | 26 | 4 | 0.00 | 5.00 | 0.00 |
| 4 | 4 | 26 | 23 | 0.00 | 5.00 | 0.00 |
| 4 | 4 | 26 | 27 | 0.00 | 5.00 | 0.00 |
| 4 | 4 | 27 | 27 | −0.30 | 3.80 | 0.00 |
| 4 | 26 | 4 | 5 | 0.00 | 5.00 | 0.00 |
| 4 | 26 | 4 | 26 | 0.00 | 5.00 | 0.00 |
| 4 | 26 | 27 | 27 | 0.00 | 5.00 | 0.00 |
| 4 | 27 | 2 | 5 | −0.30 | 3.80 | 0.00 |
| 4 | 27 | 27 | 26 | −0.30 | 3.80 | 0.00 |
| 5 | 1 | 1 | 5 | 0.00 | 0.00 | 0.24 |
| 5 | 1 | 1 | 6 | 0.00 | 0.00 | 0.50 |
| 5 | 1 | 1 | 8 | 0.00 | 0.49 | 0.16 |
| 5 | 1 | 1 | 9 | 0.00 | 0.49 | 0.16 |
| 5 | 1 | 1 | 13 | 0.00 | 0.00 | 0.40 |
| 5 | 1 | 1 | 15 | 0.00 | 0.00 | 0.40 |
| 5 | 1 | 1 | 19 | 0.00 | 0.00 | 0.30 |
| 5 | 1 | 3 | 7 | 0.00 | 0.00 | −0.04 |
| 5 | 1 | 3 | 9 | 0.00 | 0.00 | −0.04 |
| 5 | 1 | 3 | 11 | 0.00 | 0.00 | −0.09 |
| 5 | 1 | 3 | 12 | 0.00 | 0.00 | −0.06 |
| 5 | 1 | 4 | 26 | 0.00 | 0.00 | 0.10 |
| 5 | 1 | 4 | 27 | 0.00 | 0.00 | 0.10 |
| 5 | 1 | 6 | 21 | 0.00 | 0.00 | 0.30 |
| 5 | 1 | 8 | 23 | 0.00 | 0.00 | 0.30 |
| 5 | 1 | 9 | 14 | 0.00 | 0.00 | 0.06 |
| 5 | 1 | 13 | 23 | 0.00 | 0.00 | 0.20 |
| 5 | 1 | 15 | 15 | 0.00 | 0.00 | 0.80 |
| 5 | 1 | 15 | 25 | 0.00 | 0.00 | 0.50 |
| 5 | 1 | 19 | 23 | 0.00 | 0.00 | 0.05 |
| 5 | 2 | 2 | 5 | −0.30 | 3.80 | 0.00 |
| 5 | 2 | 2 | 6 | −0.30 | 3.80 | 0.00 |
| 5 | 2 | 2 | 27 | 0.00 | 3.50 | 0.00 |
| 5 | 2 | 27 | 26 | 0.00 | 3.50 | 0.00 |
| 5 | 2 | 27 | 27 | 0.00 | 3.50 | 0.00 |
| 5 | 3 | 9 | 14 | 0.00 | 2.33 | 0.0 |
| 5 | 4 | 4 | 26 | 0.00 | 3.50 | 0.00 |
| 5 | 4 | 4 | 27 | 0.00 | 3.50 | 0.00 |
| 5 | 4 | 26 | 23 | 0.00 | 5.00 | 0.00 |
| 5 | 4 | 26 | 27 | 0.00 | 5.00 | 0.00 |
| 6 | 1 | 1 | 8 | 0.00 | 0.00 | 0.06 |
| 6 | 1 | 1 | 9 | 0.00 | 0.00 | 0.06 |
| 6 | 1 | 1 | 13 | 0.00 | 0.00 | 0.06 |
| 7 | 3 | 1 | 8 | 0.00 | 0.00 | −0.04 |
| 7 | 3 | 1 | 9 | 0.00 | 0.00 | −0.04 |
| 7 | 3 | 1 | 13 | 0.00 | 0.00 | −0.04 |
| 7 | 3 | 9 | 14 | 0.00 | 2.66 | 0.00 |
| 7 | 3 | 12 | 24 | 0.00 | 0.00 | 3.10 |
| 8 | 1 | 1 | 15 | 0.00 | 0.00 | 0.06 |
| 8 | 1 | 3 | 9 | 0.00 | 0.00 | −0.09 |
| 8 | 1 | 3 | 11 | 0.00 | 0.00 | −0.09 |
| 8 | 1 | 3 | 12 | 0.00 | 0.00 | −0.06 |
| 9 | 1 | 1 | 15 | 0.00 | 0.00 | 0.06 |
| 9 | 1 | 3 | 9 | 0.00 | 0.00 | −0.04 |
| 9 | 1 | 3 | 11 | 0.00 | 0.00 | −0.09 |
| 9 | 1 | 3 | 12 | 0.00 | 0.00 | −0.06 |
| 9 | 3 | 1 | 13 | 0.00 | 0.00 | −0.06 |
| 11 | 3 | 1 | 13 | 0.00 | 0.00 | −0.09 |
| 12 | 3 | 1 | 13 | 0.00 | 0.00 | −0.06 |
| 13 | 1 | 1 | 15 | 0.15 | 0.00 | 0.10 |
| 19 | 2 | 19 | 23 | 0.00 | 4.50 | 0.00 |
| 19 | 2 | 8 | 23 | 0.00 | 4.50 | 0.00 * |
| 23 | 19 | 2 | 8 | 0.00 | 4.50 | 0.00 * |
| 23 | 26 | 4 | 26 | 0.00 | 5.00 | 0.00 |
| 23 | 26 | 27 | 27 | 0.00 | 5.00 | 0.00 |
| 26 | 4 | 4 | 26 | −0.30 | 3.80 | 0.00 |
| 26 | 4 | 4 | 27 | 0.00 | 3.80 | 0.0 |
| 1 | 1 | | | 4.40 | 1.525 | 1.510 FC ST |
| 1 | 2 | | | 4.48 | 1.504 | |
| 1 | 3 | | | 4.75 | 1.526 | |
| 1 | 4 | | | 4.40 | 1.504 | |
| 1 | 5 | | | 4.60 | 1.081 | |
| 1 | 6 | | | 5.36 | 1.425 | |
| 1 | 8 | | | 5.10 | 1.461 | |
| 1 | 9 | | | 5.47 | 1.452 | |
| 1 | 13 | | | 5.15 | 1.472 | |
| 1 | 15 | | | 3.21 | 1.815 | |
| 1 | 19 | | | 5.27 | 1.460 | * |
| 5 | 6 | | | 4.60 | 0.968 | |
| 2 | 2 | | | 9.60 | 1.382 | |
| 2 | 5 | | | 4.60 | 1.101 | |
| 2 | 6 | | | 6.20 | 1.381 | |
| 2 | 8 | | | 5.10 | 1.331 | * |

TABLE 1-continued

PEPCON

| | | | | | | |
|---|---|---|---|---|---|---|
| 2 | 19 | 5.10 | 1.331 | | | |
| 2 | 27 | 6.51 | 1.400 | | | |
| 3 | 5 | 4.8 | 1.103 | | | |
| 3 | 6 | 5.05 | 1.330 | | | |
| 3 | 7 | 10.01 | 1.229 | | | |
| 3 | 9 | 7.74 | 1.330 | | | |
| 3 | 11 | 5.11 | 1.250 | | | |
| 3 | 12 | 5.05 | 1.328 | | | |
| 6 | 21 | 4.60 | 0.968 | | | |
| 4 | 4 | 7.19 | 1.371 | | | |
| 4 | 5 | | 4.60 | 1.101 | | |
| 4 | 26 | 5.69 | 1.394 | | | |
| 4 | 27 | 5.39 | 1.459 | | | |
| 8 | 23 | 6.10 | 1.015 | | | |
| 9 | 14 | 5.78 | 0.991 | | | |
| 12 | 24 | 7.20 | 0.972 | | | |
| 13 | 23 | 6.03 | 1.023 | | | |
| 15 | 15 | 3.10 | 2.024 | | | |
| 15 | 25 | 3.80 | 1.354 | | | |
| 19 | 23 | 5.95 | 1.007 | | | |
| 23 | 26 | 6.05 | 1.010 | | | |
| 26 | 27 | 5.94 | 1.380 | | | |
| 27 | 27 | 6.21 | 1.419 | | | |
| 1 | 1 | | 0.000 | | BOND DIPOLE | |
| 1 | 2 | | 0.100 | | | |
| 1 | 3 | | -1.020 | | | |
| 1 | 4 | | -0.180 | | | |
| 1 | 5 | | 0.000 | | | |
| 1 | 6 | | 2.530 | | | |
| 1 | 8 | | 3.980 | | | |
| 1 | 9 | | 2.650 | | | |
| 5 | 6 | | -1.960 | | | |
| 1 | 13 | | 1.720 | | | |
| 1 | 15 | | -0.671 | | | |
| 1 | 19 | | 2.058 | | * | |
| 2 | 2 | | 0.000 | | | |
| 2 | 5 | | -0.058 | | | |
| 2 | 6 | | 0.810 | | | |
| 2 | 8 | | 4.524 | | * | |
| 2 | 19 | | 3.260 | | | |
| 2 | 27 | | -0.700 | | | |
| 3 | 5 | | 0.0 | | | |
| 3 | 6 | | 0.000 | | | |
| 3 | 7 | | 3.010 | | | |
| 3 | 9 | | 3.320 | | | |
| 3 | 11 | | 3.950 | | | |
| 3 | 12 | | 1.850 | | * | |
| 6 | 21 | | -1.960 | | | |
| 4 | 4 | | 0.000 | | | |
| 4 | 5 | | 0.000 | | | |
| 4 | 26 | | 2.120 | | | |
| 4 | 27 | | 1.120 | | | |
| 8 | 23 | | -1.410 | | | |
| 9 | 14 | | -1.810 | | | |
| 12 | 24 | | 0.000 | | | |
| 13 | 23 | | -1.350 | | | |
| 15 | 15 | | 0.000 | | | |
| 15 | 25 | | 0.000 | | | |
| 19 | 23 | | -2.270 | | | |
| 23 | 26 | | 1.430 | | | |
| 26 | 27 | | -1.030 | | | |
| 27 | 27 | | 0.000 | | | |
| | 4 | | 0.044 | | 1.940 | |
| | 11 | | 0.066 | | 1.780 | |
| | 12 | | 0.050 | | 1.740 | |
| | 13 | | 0.030 | | 1.900 | |
| | 14 | | 0.017 | | 0.930 | |
| | 19 | | 0.055 | | 1.820 | |
| | 25 | | 0.036 | | 1.250 | |
| | 26 | | 0.055 | | 1.820 | |
| | 27 | | 0.044 | | 1.940 | |
| 1 | 1 | 1 | 0.45 | 110.30 | 1 | |
| 1 | 1 | 1 | 0.45 | 111.20 | 2 | |
| 1 | 1 | 1 | 0.45 | 112.40 | 3 | |
| 1 | 1 | 2 | 0.58 | 114.00 | | |
| 1 | 1 | 3 | 0.67 | 107.80 | 1 | |
| 1 | 1 | 3 | 0.67 | 110.80 | 2 | |
| 1 | 1 | 3 | 0.67 | 112.20 | 3 | |
| 1 | 1 | 4 | 0.71 | 113.10 | | |
| 1 | 1 | 5 | 0.36 | 109.39 | | |
| 1 | 1 | 6 | | 0.56 | 109.10 | 1 |
| 1 | 1 | 6 | 0.56 | 104.10 | 2 | |
| 1 | 1 | 6 | 0.56 | 109.40 | 3 | |
| 1 | 1 | 8 | 0.57 | 109.47 | | |
| 1 | 1 | 9 | 0 56 | 109.40 | 1 | |
| 1 | 1 | 9 | 0.56 | 109.60 | 2 | |
| 1 | 1 | 9 | 0.85 | 111.10 | 3 | |
| 1 | 1 | 13 | 0.90 | 111.20 | | |
| 1 | 1 | 15 | 0.63 | 108.80 | | |
| 1 | 1 | 19 | 0.75 | 111.20 | | |
| 1 | 2 | 2 | 0.55 | 121.40 | | |
| 1 | 2 | 5 | 0.36 | 118.20 | | |
| 1 | 3 | 7 | 0.86 | 120.60 | | |
| 1 | 3 | 9 | 0.78 | 116.40 | | |
| 1 | 3 | 11 | 0.64 | 117.00 | | |
| 1 | 3 | 12 | 0.70 | 115.00 | | |
| 1 | 4 | 4 | 0.80 | 129.80 | | |
| 1 | 4 | 26 | 0.80 | 121.70 | | |
| 1 | 4 | 27 | 0.80 | 128.60 | | |
| 1 | 6 | 21 | 0.35 | 108.40 | | |
| 1 | 8 | 23 | 0.48 | 109.50 | | |
| 1 | 9 | 1 | 0.45 | 111.90 | | |
| 1 | 9 | 2 | 0.75 | 123.20 | | |
| 1 | 9 | 3 | 0.49 | 120.60 | 1 | |
| 1 | 9 | 3 | 0.35 | 121.70 | 2 | |
| 1 | 9 | 14 | 0.54 | 124.00 | | |
| 1 | 13 | 23 | 0.40 | 109.50 | | |
| 1 | 15 | 1 | 0.78 | 97.60 | | |
| 1 | 15 | 15 | 1.17 | 103.90 | | |
| 1 | 15 | 25 | 0.48 | 96.00 | | |
| 1 | 19 | 2 | 0.56 | 123.20 | | |
| 1 | 19 | 23 | 0.38 | 118.40 | | |
| 2 | 1 | 3 | 0.47 | 110.2 | | |
| 2 | 1 | 5 | 0.36 | 109.40 | | |
| 2 | 2 | 2 | 0.43 | 120.00 | | |
| 2 | 2 | 5 | 0.36 | 120.00 | | |
| 2 | 2 | 6 | 0.75 | 121.00 | | |
| 2 | 2 | 27 | 0.96 | 120.00 | | |
| 2 | 6 | 21 | 0.35 | 113.00 | | |
| 2 | 8 | 23 | 0.50 | 120.00 | | |
| 2 | 9 | 23 | 0.50 | 120.00 | | |
| 2 | 19 | 23 | 0.38 | 120.00 | | |
| 2 | 27 | 4 | 0.90 | 134.90 | | |
| 2 | 27 | 26 | 0.35 | 132.80 | | |
| 2 | 27 | 27 | 0.90 | 122.70 | | |
| 3 | 1 | 5 | 0.37 | 107.90 | | |
| 3 | 1 | 8 | 0.82 | 110.74 | | |
| 3 | 1 | 9 | 0.44 | 110.00 | 1 | |
| 3 | 1 | 9 | 0.47 | 109.70 | 2 | |
| 3 | 1 | 9 | 0.56 | 110.80 | 3 | |
| 3 | 1 | 13 | 0.90 | 110.74 | | |
| 3 | 9 | 14 | 0.50 | 122.50 | | |
| 3 | 12 | 24 | 0.74 | 106.10 | | |
| 4 | 1 | 5 | 0.38 | 109.50 | | |
| 4 | 4 | 5 | 0.36 | 126.30 | | |
| 4 | 4 | 26 | 0.80 | 107.90 | | |
| 4 | 4 | 27 | 0.43 | 106.40 | | |
| 4 | 26 | 4 | 0.80 | 106.30 | | |
| 4 | 26 | 23 | 0.40 | 126.40 | | |
| 4 | 26 | 27 | 0.80 | 111.60 | | |
| 4 | 27 | 27 | 0.95 | 108.80 | | |
| 5 | 1 | 5 | 0.32 | 109.40 | | |
| 5 | 1 | 6 | 0.43 | 103.10 | | |
| 5 | 1 | 8 | 0.46 | 108.80 | | |
| 5 | 1 | 9 | 0.36 | 109.39 | 1 | |
| 5 | 1 | 9 | 0.36 | 109.41 | 2 | |
| 5 | 1 | 9 | 0.36 | 110.00 | 3 | |
| 5 | 1 | 13 | 0.50 | 108.80 | | |
| 5 | 1 | 15 | 0.36 | 112.00 | | |
| 5 | 1 | 19 | 0.38 | 109.00 | | * |
| 5 | 2 | 27 | 0.36 | 120.00 | | |
| 5 | 3 | 7 | 0.37 | 112.0 | | |
| 5 | 3 | 9 | 0.40 | 122.3 | | |
| 5 | 4 | 26 | 0.36 | 120.00 | | |

TABLE 1-continued

PEPCON

| | | | | |
|---|---|---|---|---|
| 7 | 3 | 9 | 0.85 | 124.10 |
| 7 | 3 | 12 | 1.13 | 124.50 |
| 8 | 2 | 19 | 0.80 | 120.00 |
| 11 | 3 | 11 | 0.85 | 126.00 |
| 14 | 9 | 14 | 0.50 | 120.00 |
| 19 | 2 | 19 | 0.80 | 120.00 |
| 23 | 8 | 23 | 0.50 | 106.80 |
| 23 | 19 | 23 | 0.50 | 120.00 |
| 23 | 13 | 23 | 0.50 | 109.50 |
| 23 | 26 | 27 | 0.40 | 124.20 |
| 26 | 4 | 26 | 0.90 | 110.90 |
| 26 | 27 | 27 | 0.90 | 104.40 |
| 1 | 6 | 5 | 0.35 | 108.40 |
| 9 | 1 | 6 | 0.62 | 111.00 |
| | 3 | 11 | 0.8 | |
| | 3 | 12 | 0.8 | |
| | 9 | 14 | 0.05 | |
| | 2 | 27 | 0.05 | |
| | 2 | 1 | 0.05 | |
| | 2 | 2 | 0.05 | |
| | 2 | 5 | 0.05 | |
| | 2 | 6 | 0.05 | |
| | 2 | 8 | 0.05 | |
| | 2 | 19 | 0.05 | |
| | 3 | 1 | 0.8 | |
| | 3 | 5 | 0.8 | |
| | 3 | 7 | 0.8 | |
| | 3 | 9 | 0.8 | |
| | 9 | 1 | 0.05 | |
| | 9 | 3 | 0.05 | |
| | 4 | 26 | 0.05 | |
| | 4 | 4 | 0.05 | |
| | 27 | 27 | 0.05 | |
| | 27 | 2 | 0.05 | |
| | 27 | 4 | 0.05 | |
| | 26 | 27 | 0.05 | |
| | 4 | 1 | 0.05 | |
| | 4 | 5 | 0.05 | |
| | 4 | 27 | 0.05 | |
| | 27 | 26 | 0.05 | |

ADDED O.P.A. (MM2)

*KY
*KY

TABLE 2

PENCON

| | | | | | | |
|---|---|---|---|---|---|---|
| 117 | 25 | 6 | 70 | 25 | | |
| 1 | 1 | 3 | 6 | 0.40 | −0.30 | −0.07 |
| 1 | 3 | 9 | 20 | 1.80 | 6.49 | −6.23 |
| 1 | 6 | 2 | 2 | 2.30 | −2.53 | |
| 1 | 6 | 3 | 7 | −1.66 | 8.98 | 0.00 |
| 1 | 6 | 3 | 16 | −2.50 | 1.39 | 0.00 |
| 1 | 8 | 20 | 5 | 0.00 | 0.00 | 0.52 |
| 1 | 8 | 20 | 22 | −0.20 | 0.73 | 0.80 |
| 1 | 8 | 20 | 26 | 0.00 | 0.00 | 0.00 |
| 1 | 16 | 1 | 5 | 0.00 | 0.00 | 0.27 |
| 1 | 16 | 15 | 22 | −1.00 | 3.01 | 1.86 |
| 1 | 16 | 16 | 3 | −0.26 | 1.00 | −0.80 |
| 1 | 16 | 16 | 5 | 0.00 | 0.00 | −0.90 |
| 1 | 16 | 16 | 27 | −0.26 | 0.70 | −0.06 |
| 1 | 25 | 6 | 19 | 0.00 | 0.00 | 0.00 |
| 1 | 25 | 25 | 25 | 0.00 | 3.50 | 0.00 |
| 2 | 1 | 3 | 9 | 0.00 | −0.50 | −1.70 |
| 2 | 2 | 1 | 3 | 0.00 | 0.00 | 0.50 |
| 2 | 2 | 2 | 6 | 0.00 | 3.80 | 0.00 |
| 2 | 2 | 2 | 25 | −0.30 | 3.50 | 0.00 |
| 2 | 2 | 25 | 19 | 0.00 | 1.00 | 0.30 |
| 2 | 2 | 25 | 25 | 0.00 | 1.00 | 0.30 |
| 2 | 6 | 1 | 3 | 0.00 | 0.00 | −0.60 |
| 2 | 6 | 1 | 5 | 0.00 | 0.00 | 0.53 |
| 2 | 25 | 19 | 6 | 0.00 | 4.50 | 0.00 |
| 2 | 25 | 25 | 3 | 0.00 | 3.50 | 0.00 |
| 3 | 6 | 1 | 6 | −1.00 | −5.00 | 0.00 |
| 3 | 9 | 20 | 5 | 0.00 | 0.00 | 0.51 |
| 3 | 9 | 20 | 22 | 0.00 | 0.00 | 0.01 |
| 3 | 9 | 20 | 26 | −3.50 | −0.05 | −4.30 |

TABLE 2-continued

PENCON

| | | | | | | |
|---|---|---|---|---|---|---|
| 3 | 16 | 16 | 15 | −1.75 | 0.60 | 1.50 |
| 3 | 16 | 27 | 22 | −1.00 | −0.80 | 0.40 |
| 3 | 16 | 27 | 26 | −1.00 | −0.53 | 1.13 |
| 3 | 25 | 25 | 1 | 0.00 | 5.00 | 0.00 |
| 3 | 25 | 25 | 6 | 0.00 | 3.80 | 0.00 |
| 3 | 25 | 25 | 19 | 0.00 | 3.80 | 0.00 |
| 5 | 1 | 16 | 15 | 0.00 | 0.00 | 0.40 |
| 5 | 1 | 16 | 16 | 0.00 | 0.00 | 0.27 |
| 5 | 1 | 25 | 6 | 0.00 | 0.00 | 0.54 |
| 5 | 1 | 25 | 25 | 0.00 | 0.00 | 0.05 |
| 5 | 2 | 2 | 6 | −0.30 | 3.80 | 0.00 |
| 5 | 2 | 2 | 25 | 0.00 | 3.50 | 0.00 |
| 5 | 16 | 3 | 6 | 0.00 | 0.00 | −0.02 |
| 5 | 16 | 3 | 7 | 0.00 | 0.00 | −0.04 |
| 5 | 16 | 3 | 29 | 0.00 | 0.00 | −0.04 |
| 5 | 16 | 3 | 30 | 0.00 | 0.00 | −0.09 |
| 5 | 16 | 16 | 15 | 0.00 | 0.00 | −0.80 |
| 5 | 16 | 27 | 22 | 0.00 | 0.00 | 0.40 |
| 5 | 16 | 27 | 26 | 0.00 | 0.00 | 0.04 |
| 5 | 20 | 9 | 14 | 0.00 | 0.00 | 0.00 |
| 5 | 20 | 22 | 5 | 0.00 | 0.00 | 1.30 |
| 5 | 20 | 22 | 15 | 0.00 | 0.00 | 0.04 |
| 5 | 20 | 22 | 27 | 0.00 | 0.00 | 0.10 |
| 5 | 20 | 26 | 27 | 0.00 | 0.00 | −0.09 |
| 5 | 20 | 26 | 28 | 0.00 | 0.00 | 0.21 |
| 5 | 22 | 15 | 16 | 0.00 | 0.00 | 0.00 |
| 5 | 22 | 20 | 8 | 0.00 | 0.00 | 0.20 |
| 5 | 22 | 20 | 9 | 0.00 | 0.00 | 0.20 |
| 5 | 22 | 20 | 12 | 0.00 | 3.00 | 0.40 |
| 5 | 22 | 20 | 13 | 0.00 | 5.00 | 0.20 |
| 5 | 22 | 20 | 26 | 0.00 | 0.00 | 0.87 |
| 5 | 22 | 27 | 16 | 0.00 | 0.00 | 0.00 |
| 5 | 22 | 27 | 26 | 0.00 | 0.00 | 0.98 |
| 6 | 1 | 3 | 7 | 0.00 | 0.00 | −0.04 |
| 6 | 1 | 3 | 9 | 0.00 | 0.00 | −0.04 |
| 6 | 3 | 16 | 16 | 0.40 | −0.30 | −0.07 |
| 6 | 3 | 16 | 27 | 0.00 | 0.00 | 0.50 |
| 6 | 19 | 25 | 25 | 0.00 | 4.50 | 0.00 |
| 6 | 25 | 25 | 25 | 0.00 | 3.80 | 0.00 |
| 7 | 3 | 9 | 20 | 0.00 | 7.19 | 0.00 |
| 7 | 3 | 16 | 16 | 0.00 | 0.00 | −0.04 |
| 7 | 3 | 16 | 27 | 0.00 | 0.00 | −0.04 |
| 7 | 3 | 25 | 25 | 4.00 | 0.40 | 2.40 |
| 9 | 3 | 25 | 25 | 4.30 | 0.40 | 2.90 |
| 8 | 20 | 22 | 27 | 0.00 | 0.00 | 0.40 |
| 8 | 20 | 26 | 27 | −4.30 | 5.00 | −1.50 |
| 8 | 20 | 26 | 28 | −3.50 | 3.00 | 8.00 |
| 9 | 20 | 22 | 15 | 0.50 | 0.00 | 1.00 |
| 9 | 20 | 22 | 27 | 0.00 | 0.00 | 0.40 |
| 9 | 20 | 26 | 27 | −4.30 | 5.00 | −1.50 |
| 9 | 20 | 26 | 28 | −3.50 | 3.00 | 8.00 |
| 12 | 20 | 22 | 15 | 0.00 | 0.00 | 0.04 |
| 12 | 20 | 22 | 27 | 0.00 | 0.00 | 0.50 |
| 12 | 20 | 26 | 27 | 0.00 | 0.00 | −0.09 |
| 12 | 20 | 26 | 28 | 0.00 | 0.00 | 0.21 |
| 13 | 20 | 22 | 15 | 0.50 | −2.75 | 3.00 |
| 13 | 20 | 22 | 27 | 0.00 | 0.00 | 1.40 |
| 13 | 20 | 26 | 27 | −4.30 | 5.00 | −1.50 |
| 13 | 20 | 26 | 28 | −1.50 | 5.00 | 8.00 |
| 14 | 9 | 3 | 25 | 0.00 | 2.66 | 0.00 |
| 14 | 9 | 20 | 22 | 0.00 | 0.00 | 0.01 |
| 14 | 9 | 20 | 26 | 0.00 | 0.00 | 0.01 |
| 15 | 16 | 16 | 27 | −0.75 | 2.00 | −0.90 |
| 15 | 22 | 20 | 26 | 0.00 | 1.00 | 1.00 |
| 15 | 22 | 27 | 16 | −3.00 | 7.00 | 0.00 |
| 15 | 22 | 27 | 26 | 0.00 | 1.00 | 0.30 |
| 16 | 15 | 22 | 20 | −2.50 | 3.60 | −3.00 |
| 16 | 15 | 22 | 27 | −2.50 | 3.00 | −1.00 |
| 16 | 16 | 3 | 29 | 0.00 | 0.00 | −0.20 |
| 16 | 16 | 3 | 30 | 0.00 | 0.00 | −0.09 |
| 16 | 16 | 15 | 22 | 0.00 | 2.50 | 0.40 |
| 16 | 16 | 27 | 22 | −1.00 | −2.50 | 0.40 |
| 16 | 16 | 27 | 26 | −0.50 | 0.50 | 2.50 |
| 16 | 27 | 22 | 20 | 0.00 | 1.00 | −0.50 |
| 16 | 27 | 26 | 20 | −4.00 | 3.00 | 0.40 |
| 16 | 27 | 26 | 28 | −1.00 | 3.00 | 2.00 |
| 19 | 6 | 25 | 25 | 0.00 | 3.50 | 0.00 |

TABLE 2-continued

PENCON

| | | | | | | | | |
|---|---|---|---|---|---|---|---|---|
| | 19 | 25 | 25 | 25 | 0.00 | | 3.80 | 0.00 |
| | 20 | 9 | 3 | 25 | 1.80 | | 6.49 | -5.23 |
| 4 | 20 | 22 | 27 | 26 | 1.50 | | 10.00 | 1.00 |
| 4 | 20 | 26 | 27 | 22 | -1.00 | | 8.50 | 5.00 |
| 4 | 22 | 20 | 26 | 27 | -1.00 | | 9.00 | 3.00 |
| | 22 | 20 | 26 | 28 | 0.20 | | 3.50 | -2.50 |
| | 22 | 27 | 26 | 28 | 0.20 | | 8.00 | -4.70 |
| | 25 | 6 | 19 | 25 | 0.00 | | 3.50 | 0.00 |
| 4 | 26 | 20 | 22 | 27 | -2.65 | | 6.10 | 0.20 |
| | 27 | 16 | 3 | 29 | 0.00 | | 0.00 | -0.06 |
| | 27 | 16 | 3 | 30 | 0.00 | | 0.00 | -0.09 |
| | | 1 | 16 | | 5.26 | 1.525 | | |
| | | 1 | 25 | | 5.48 | 1.512 | | |
| | | 2 | 25 | | 9.60 | 1.526 | | |
| | | 3 | 16 | | 4.45 | 1.550 | | |
| | | 3 | 25 | | 9.60 | 1.332 | | |
| | | 5 | 16 | | 4.60 | 1.070 | | |
| | | 5 | 20 | | 4.39 | 1.080 | | |
| | | 5 | 22 | | 4.38 | 1.090 | | |
| | | 6 | 19 | | 4.32 | 1.410 | | |
| | | 6 | 25 | | 4.09 | 1.350 | | |
| | | 8 | 20 | | 5.10 | 1.510 | | |
| | | 9 | 20 | | 5.47 | 1.449 | | |
| | | 12 | 20 | | 3.23 | 1.793 | | |
| | | 13 | 20 | | 2.30 | 1.926 | | |
| | | 15 | 16 | | 3.98 | 1.851 | | |
| | | 15 | 22 | | 3.98 | 1.810 | | |
| | | 16 | 16 | | 4.50 | 1.565 | | |
| | | 16 | 27 | | 4.30 | 1.476 | | |
| | | 19 | 25 | | 6.50 | 1.310 | | |
| | | 20 | 22 | | 2.56 | 1.553 | | |
| | | 20 | 26 | | 2.58 | 1.527 | | |
| | | 20 | 27 | | 4.30 | 1.484 | | |
| | | 25 | 25 | | 5.83 | 1.380 | | |
| | | 26 | 27 | | 4.79 | 1.393 | | |
| | | 26 | 28 | | 8.65 | 1.201 | | |
| | | 1 | 16 | | 0.000 | | | |
| | | 1 | 25 | | 0.100 | | | |
| | | 2 | 25 | | 0.000 | | | |
| | | 3 | 16 | | 5.872 | | | |
| | | 3 | 25 | | 0.000 | | | |
| | | 5 | 16 | | 0.000 | | | |
| | | 5 | 20 | | 0.000 | | | |
| | | 5 | 22 | | 0.000 | | | |
| | | 6 | 19 | | 0.081 | | | |
| | | 6 | 25 | | 0.212 | | | |
| | | 8 | 20 | | 3.980 | | | |
| | | 9 | 20 | | 0.000 | | | |
| | | 12 | 20 | | 1.940 | | | |
| | | 13 | 20 | | 1.790 | | | |
| | | 15 | 16 | | 4.464 | | | |
| | | 15 | 22 | | 3.653 | | | |
| | | 16 | 16 | | 0.000 | | | |
| | | 16 | 27 | | 2.304 | | | |
| | | 19 | 25 | | 0.330 | | | |
| | | 25 | 25 | | 0.000 | | | |
| | | 20 | 22 | | -0.062 | | | |
| | | 20 | 26 | | 1.547 | | | |
| | | 22 | 27 | | 0.712 | | | |
| | | 26 | 27 | | 2.280 | | | |
| | | 26 | 28 | | 1.533 | | | |
| | | | 16 | | 0.044 | 1.920 | | |
| | | | 20 | | 0.044 | 1.920 | | |
| | | | 25 | | 0.044 | 1.920 | | |
| | | | 26 | | 0.044 | 1.920 | | |
| | | | 27 | | 0.055 | 1.820 | | |
| | | | 28 | | 0.066 | 1.740 | | |
| | | 1 | 6 | 2 | | 0.77 | 117.00 | |
| | | 1 | 8 | 20 | | 0.63 | 110.00 | |
| | | 1 | 16 | 1 | | 0.45 | 110.90 | 1 |
| | | 1 | 16 | 1 | | 0.45 | 111.20 | 2 |
| | | 1 | 16 | 1 | | 0.45 | 112.40 | 3 |
| | | 1 | 16 | 5 | | 0.36 | 109.40 | |
| | | 1 | 16 | 15 | | 0.63 | 109.80 | |
| | | 1 | 16 | 16 | | 0.45 | 110.30 | 1 |
| | | 1 | 16 | 16 | | 0.45 | 111.20 | 2 |

TABLE 2-continued

PENCON

| | | | | | | |
|---|---|---|---|---|---|---|
| | 1 | 16 | 16 | 0.45 | 112.40 | 3 |
| | 1 | 25 | 6 | 0.50 | 117.00 | |
| | 1 | 25 | 25 | 0.55 | 134.00 | |
| | 2 | 2 | 25 | 0.43 | 120.00 | |
| | 2 | 25 | 19 | 0.43 | 120.00 | |
| | 2 | 25 | 25 | 0.43 | 128.00 | |
| | 3 | 1 | 6 | 0.70 | 106.00 | |
| | 3 | 9 | 20 | 0.49 | 121.20 | |
| | 3 | 16 | 5 | 0.37 | 107.90 | |
| | 3 | 16 | 16 | 0.67 | 113.90 | |
| | 3 | 16 | 27 | 0.44 | 111.30 | |
| | 3 | 25 | 25 | 0.60 | 129.00 | |
| | 5 | 1 | 16 | 0.36 | 109.40 | |
| | 5 | 1 | 25 | 0.36 | 109.40 | |
| | 5 | 16 | 15 | 0.36 | 112.00 | |
| | 5 | 16 | 16 | 0.36 | 113.36 | |
| | 5 | 16 | 27 | 0.50 | 100.00 | |
| | 5 | 20 | 8 | 0.36 | 98.90 | |
| | 5 | 20 | 9 | 0.36 | 98.90 | |
| | 5 | 20 | 22 | 0.33 | 113.50 | |
| | 5 | 20 | 26 | 0.63 | 113.50 | |
| | 5 | 22 | 15 | 0.36 | 112.00 | |
| | 5 | 22 | 20 | 0.45 | 119.30 | |
| | 5 | 22 | 27 | 0.37 | 112.40 | |
| | 6 | 3 | 16 | 0.65 | 107.10 | |
| | 6 | 19 | 25 | 0.90 | 106.00 | |
| | 6 | 25 | 25 | 1.38 | 109.00 | |
| | 7 | 3 | 25 | 0.50 | 118.00 | |
| | 7 | 3 | 16 | 0.86 | 110.60 | |
| | 8 | 20 | 22 | 0.56 | 117.30 | |
| | 8 | 20 | 26 | 0.56 | 115.00 | |
| | 9 | 3 | 25 | 0.50 | 115.00 | |
| | 9 | 20 | 22 | 0.56 | 118.70 | |
| | 9 | 20 | 26 | 0.56 | 116.50 | |
| | 12 | 20 | 13 | 1.03 | 111.11 | |
| | 12 | 20 | 22 | 0.35 | 115.30 | |
| | 12 | 20 | 26 | 0.35 | 114.70 | |
| | 13 | 20 | 22 | 0.36 | 117.70 | |
| | 13 | 20 | 26 | 0.36 | 110.50 | |
| | 14 | 9 | 20 | 0.54 | 137.90 | |
| | 15 | 16 | 16 | 0.95 | 104.10 | |
| | 15 | 22 | 20 | 0.63 | 119.50 | |
| | 15 | 22 | 27 | 0.95 | 104.10 | |
| | 16 | 15 | 22 | 1.10 | 93.00 | |
| | 16 | 16 | 27 | 0.95 | 105.70 | |
| | 16 | 27 | 22 | 0.70 | 117.40 | |
| | 16 | 27 | 26 | 0.95 | 126.10 | |
| | 19 | 6 | 25 | 0.71 | 109.00 | |
| | 19 | 25 | 25 | 1.46 | 111.00 | |
| 4 | 20 | 22 | 27 | 0.27 | 87.50 | |
| 4 | 20 | 26 | 27 | 0.52 | 92.20 | |
| | 20 | 26 | 28 | -0.02 | 136.80 | |
| 4 | 22 | 20 | 26 | 0.30 | 85.20 | |
| 4 | 22 | 27 | 26 | 0.35 | 93.40 | |
| | 27 | 26 | 28 | 1.59 | 130.60 | |
| | | 2 | 25 | 0.05 | | |
| | | 3 | 16 | 0.80 | | |
| | | 3 | 25 | 0.80 | | |
| | | 9 | 20 | 0.05 | | |
| | | 20 | 26 | 0.80 | | |
| | | 26 | 27 | 0.80 | | |

TABLE 3

CEPARAM

| | | | | | | | |
|---|---|---|---|---|---|---|---|
| | 125 | 19 | 6 | 68 | 18 | | 78.5 |
| 1 | | 3 | 16 | 16 | 0.34 | 11.10 | 0.00 |
| 1 | | 3 | 16 | 32 | 0.00 | 0.00 | -0.09 |
| 1 | | 3 | 9 | 20 | 1.80 | 6.49 | -6.23 |
| 1 | | 6 | 2 | 2 | 3.53 | 2.30 | -2.53 |
| 1 | | 8 | 20 | 5 | 0.00 | 0.00 | 0.52 |
| 1 | | 8 | 20 | 22 | -0.20 | 0.73 | 0.80 |
| 1 | | 8 | 20 | 31 | 0.00 | 0.00 | 0.00 |

TABLE 3-continued

CEPARAM

| | | | | | | | | | | | | | | |
|---|---|---|---|---|---|---|---|---|---|---|---|---|---|---|
| 1 | 15 | 22 | 5 | 0.00 | 0.00 | 0.00 | | 12 | 20 | 22 | 15 | 0.00 | 0.00 | 0.04 |
| 1 | 15 | 22 | 20 | 2.50 | 3.60 | 0.00 | | 12 | 20 | 22 | 32 | 0.00 | 0.00 | 0.50 |
| 1 | 15 | 22 | 32 | 2.50 | 3.00 | 1.00 | | 12 | 20 | 31 | 32 | 0.00 | 0.00 | −0.09 |
| 1 | 16 | 1 | 5 | 0.00 | 0.00 | 0.27 | | 12 | 20 | 31 | 28 | 0.00 | 0.00 | 0.21 |
| 1 | 16 | 1 | 15 | 1.68 | 1.11 | −0.20 | | 13 | 20 | 22 | 15 | 0.50 | −2.75 | 3.00 |
| 1 | 16 | 1 | 32 | 0.00 | 0.00 | 1.40 | | 13 | 20 | 22 | 32 | 0.00 | 0.00 | 1.40 |
| 1 | 16 | 15 | 22 | −1.00 | 3.01 | 1.86 | | 13 | 20 | 31 | 32 | −4.30 | 5.00 | −1.50 |
| 1 | 16 | 16 | 3 | 0.00 | 15.00 | 0.00 | | 13 | 20 | 31 | 28 | −1.50 | 5.00 | 8.00 |
| 1 | 16 | 16 | 5 | 0.00 | 0.00 | −0.90 | | 14 | 9 | 20 | 22 | 0.00 | 0.00 | 0.01 |
| 1 | 16 | 16 | 15 | −0.45 | 27.10 | −0.78 | | 14 | 9 | 20 | 26 | 0.00 | 0.00 | 0.01 |
| 1 | 16 | 16 | 32 | 0.00 | 15.00 | 0.00 | | 14 | 9 | 20 | 31 | 0.00 | 0.00 | 0.01 |
| 1 | 20 | 9 | 3 | 0.00 | 0.00 | 0.06 | | 15 | 1 | 16 | 16 | 1.68 | 1.10 | −0.33 |
| 1 | 20 | 22 | 5 | 0.0 | 0.0 | 2.0 | | 15 | 16 | 16 | 32 | −0.75 | 2.00 | −0.90 |
| 1 | 20 | 22 | 27 | 0.00 | 0.00 | 0.10 | | 15 | 22 | 20 | 31 | 0.00 | 1.00 | 1.00 |
| 1 | 20 | 26 | 27 | 0.0 | 0.00 | −0.09 | | 15 | 22 | 32 | 16 | −3.00 | 7.00 | 0.00 |
| 1 | 20 | 26 | 28 | 0.0 | 0.00 | 0.27 | | 15 | 22 | 32 | 31 | 0.00 | 1.00 | 0.30 |
| 1 | 32 | 22 | 15 | 4.97 | 6.13 | 5.47 | | 16 | 1 | 3 | 30 | 0.00 | 0.00 | −0.35 |
| 1 | 32 | 22 | 20 | 0.0 | 1.00 | −0.56 | | 16 | 1 | 15 | 22 | 1.67 | 1.11 | −0.18 |
| 1 | 32 | 22 | 5 | 0.0 | 0.0 | 0.0 | | 16 | 1 | 32 | 22 | −1.00 | −2.50 | 0.40 |
| 1 | 32 | 31 | 20 | −4.00 | 3.00 | 0.40 | | 16 | 1 | 32 | 31 | −0.50 | 0.50 | 2.50 |
| 1 | 32 | 31 | 28 | −1.00 | 3.00 | 2.00 | | 16 | 15 | 22 | 20 | −2.50 | 3.60 | −3.00 |
| 2 | 1 | 3 | 9 | 0.00 | −0.50 | −1.70 | | 16 | 15 | 22 | 32 | −2.50 | 3.00 | −1.00 |
| 2 | 2 | 1 | 3 | 0.00 | 0.00 | 0.50 | | 16 | 16 | 1 | 3 | 0.00 | 0.00 | 0.90 |
| 2 | 6 | 1 | 3 | 0.00 | 0.00 | −0.60 | | 16 | 16 | 1 | 32 | 0. | 0. | 0. |
| 2 | 6 | 1 | 5 | 0.00 | 0.00 | 0.53 | | 16 | 16 | 3 | 29 | 0.00 | 10.00 | 0.00 |
| 3 | 1 | 16 | 1 | 0.00 | 0.00 | 0.00 | | 16 | 16 | 3 | 30 | 0.00 | 10.00 | 0.00 |
| 3 | 1 | 32 | 22 | −1.00 | −0.08 | 0.40 | | 16 | 16 | 15 | 22 | 0.00 | 2.50 | 0.40 |
| 3 | 1 | 32 | 31 | −1.00 | −0.53 | 1.13 | | 16 | 16 | 32 | 22 | 6.34 | 8.05 | 3.16 |
| 3 | 9 | 20 | 5 | 0.00 | 0.00 | 0.51 | | 16 | 16 | 32 | 31 | −3.34 | 6.00 | 0.00 |
| 3 | 9 | 20 | 22 | 0.00 | 0.00 | 0.01 | | 16 | 32 | 22 | 20 | 0.00 | 1.00 | −0.50 |
| 3 | 9 | 20 | 31 | −3.50 | −0.05 | −4.30 | | 16 | 32 | 31 | 20 | −4.00 | 3.00 | 0.40 |
| 3 | 16 | 16 | 15 | −1.75 | 0.30 | 1.50 | | 16 | 32 | 31 | 28 | −1.00 | 3.00 | 2.00 |
| 3 | 16 | 32 | 22 | −1.00 | −0.80 | 0.40 | 4 | 20 | 22 | 32 | 31 | 1.50 | 10.00 | 1.00 |
| 3 | 16 | 32 | 31 | −1.00 | −0.53 | 1.13 | 4 | 20 | 31 | 32 | 22 | −1.00 | 8.50 | 5.00 |
| 5 | 1 | 3 | 16 | 0.00 | 0.00 | 0.00 | 4 | 22 | 20 | 31 | 32 | −10.00 | 9.00 | 3.00 |
| 5 | 1 | 3 | 30 | 0.00 | 0.00 | −0.09 | | 22 | 20 | 31 | 28 | 0.20 | 3.50 | −2.50 |
| 5 | 1 | 15 | 22 | 0.00 | 0.00 | 0.00 | | 22 | 32 | 31 | 28 | 0.20 | 8.00 | −4.70 |
| 5 | 1 | 16 | 15 | 0.00 | 0.00 | 0.40 | 4 | 31 | 20 | 22 | 32 | −2.65 | 6.10 | 0.20 |
| 5 | 1 | 16 | 16 | 0.00 | 0.00 | 0.27 | | 32 | 16 | 3 | 29 | 0.00 | 0.00 | −0.06 |
| 5 | 1 | 20 | 9 | 0.00 | 0.49 | 0.16 | | 32 | 1 | 3 | 30 | 0.00 | 0.00 | −0.09 |
| 5 | 1 | 20 | 22 | 0.00 | 0.00 | 0.27 | | 32 | 16 | 3 | 30 | 0.00 | 0.00 | −0.09 |
| 5 | 1 | 20 | 26 | 0.00 | 0.00 | 0.16 | | 1 | 15 | | 3.02 | 1.806 | | |
| 5 | 1 | 32 | 22 | 0.00 | 0.00 | 0.40 | | 1 | 32 | | 4.10 | 1.449 | | |
| 5 | 1 | 32 | 31 | 0.00 | 0.00 | 0.04 | | 15 | 22 | | 2.72 | 1.752 | | |
| 5 | 16 | 3 | 7 | 0.00 | 0.00 | −0.04 | | 1 | 16 | | 4.55 | 1.486 | | |
| 5 | 16 | 3 | 29 | 0.00 | 0.00 | −0.04 | | 15 | 16 | | 3.45 | 1.790 | | |
| 5 | 16 | 3 | 30 | 0.00 | 0.00 | −0.09 | | 16 | 16 | | 10.10 | 1.310 | | |
| 5 | 16 | 15 | 22 | 0.00 | 0.00 | −0.10 | | 16 | 32 | | 5.34 | 1.413 | | |
| 5 | 16 | 16 | 15 | 0.00 | 0.00 | −0.80 | | 3 | 16 | | 3.05 | 1.550 | | |
| 5 | 16 | 32 | 22 | 0.00 | 0.00 | 0.40 | | 3 | 30 | | 10.01 | 1.240 | | |
| 5 | 16 | 32 | 31 | 0.00 | 0.00 | 0.04 | | 5 | 16 | | 5.18 | 1.101 | | |
| 5 | 20 | 9 | 14 | 0.00 | 0.00 | 0.00 | | 22 | 32 | | 4.55 | 1.413 | | |
| 5 | 20 | 22 | 5 | 0.00 | 0.00 | 1.30 | | 31 | 32 | | 4.57 | 1.396 | | |
| 5 | 20 | 22 | 15 | 0.00 | 0.00 | 0.04 | | 20 | 22 | | 4.58 | 1.564 | | |
| 5 | 20 | 22 | 32 | 0.00 | 0.00 | 0.10 | | 9 | 20 | | 5.70 | 1.449 | | |
| 5 | 20 | 31 | 32 | 0.00 | 0.00 | −0.09 | | 20 | 31 | | 4.53 | 1.527 | | |
| 5 | 20 | 31 | 28 | 0.00 | 0.00 | 0.21 | | 28 | 31 | | 12.48 | 1.199 | | |
| 5 | 22 | 15 | 16 | 0.00 | 0.00 | 0.00 | | 1 | 5 | | 4.39 | 1.081 | | |
| 5 | 22 | 20 | 8 | 0.00 | 0.00 | 0.20 | | 5 | 22 | | 4.20 | 1.081 | | |
| 5 | 22 | 20 | 9 | 0.00 | 0.00 | 0.20 | | 5 | 20 | | 4.53 | 1.081 | | |
| 5 | 22 | 20 | 12 | 0.00 | 3.00 | 0.40 | | 1 | 16 | | 0.000 | | | |
| 5 | 22 | 20 | 13 | 0.00 | 5.00 | 0.20 | | 3 | 16 | | 5.872 | | | |
| 5 | 22 | 20 | 31 | 0.00 | 0.00 | 0.87 | | 3 | 30 | | 3.950 | | | |
| 5 | 22 | 32 | 16 | 0.00 | 0.00 | 0.00 | | 5 | 20 | | 0.000 | | | |
| 5 | 22 | 32 | 31 | 0.00 | 0.00 | 0.98 | | 5 | 22 | | 0.000 | | | |
| 6 | 1 | 3 | 7 | 0.00 | 0.00 | −0.04 | | 9 | 20 | | 0.000 | | | |
| 6 | 1 | 3 | 9 | 0.00 | 0.00 | −0.04 | | 1 | 15 | | −1.347 | | | |
| 7 | 3 | 9 | 20 | 0.00 | 7.19 | 0.00 | | 15 | 22 | | 0.672 | | | |
| 7 | 3 | 16 | 16 | 0.00 | 0.00 | −0.04 | | 15 | 16 | | 0.755 | | | |
| 7 | 3 | 16 | 32 | 0.00 | 0.00 | −0.04 | | 15 | 22 | | 0.448 | | | |
| 8 | 20 | 22 | 32 | 0.00 | 0.00 | 0.40 | | 1 | 32 | | 0.756 | | | |
| 8 | 20 | 31 | 32 | −4.30 | 5.00 | −1.50 | | 16 | 16 | | 0.000 | | | |
| 8 | 20 | 31 | 28 | −3.50 | 3.00 | 8.00 | | 16 | 32 | | 1.192 | | | |
| 9 | 20 | 22 | 15 | 0.50 | 0.00 | 1.00 | | 20 | 22 | | −0.343 | | | |
| 9 | 20 | 22 | 32 | 0.00 | 0.00 | 0.40 | | 20 | 31 | | −1.628 | | | |
| 9 | 20 | 31 | 32 | −4.30 | 5.00 | −1.50 | | 22 | 32 | | 0.977 | | | |
| 9 | 20 | 31 | 28 | −3.50 | 3.00 | 8.00 | | 31 | 32 | | 2.117 | | | |

TABLE 3-continued

CEPARAM

|   |    |    |        |        |
|---|----|----|--------|--------|
|   | 28 | 31 | −1.659 |        |
|   |    | 16 | 0.044  | 1.920  |
|   |    | 20 | 0.044  | 1.920  |
|   |    | 30 | 0.066  | 1.740  |
|   |    | 31 | 0.044  | 1.920  |
|   |    | 32 | 0.055  | 1.820  |
|   |    | 28 | 0.066  | 1.740  |
|   | 1  | 3  | 16     | 0.40   | 115.00 |
|   | 1  | 3  | 30     | 0.64   | 116.50 |
|   | 1  | 6  | 2      | 0.77   | 110.80 |
|   | 1  | 8  | 20     | 0.63   | 110.00 |
|   | 1  | 15 | 22     | 0.76   | 96.00  |
|   | 1  | 16 | 1      | 0.74   | 113.90 |
|   | 1  | 16 | 1      | 0.45   | 111.20 |
|   | 1  | 16 | 1      | 0.45   | 112.40 |
|   | 1  | 16 | 5      | 0.36   | 109.40 |
|   | 1  | 16 | 15     | 0.22   | 109.80 |
|   | 1  | 16 | 16     | 1.05   | 122.00 |
|   | 1  | 32 | 22     | 0.97   | 127.00 |
|   | 2  | 32 | 31     | 0.95   | 136.70 |
|   | 3  | 1  | 6      | 0.70   | 106.00 |
|   | 3  | 1  | 32     | 0.83   | 108.40 |
|   | 3  | 9  | 20     | 0.53   | 121.20 |
|   | 3  | 16 | 5      | 0.45   | 107.90 |
|   | 3  | 16 | 16     | 0.59   | 113.90 |
|   | 3  | 16 | 32     | 0.83   | 111.30 |
|   | 5  | 1  | 16     | 0.36   | 109.40 |
|   | 5  | 1  | 5      | 0.39   | 110.60 |
|   | 5  | 1  | 15     | 0.44   | 108.30 |
|   | 5  | 1  | 16     | 0.46   | 106.00 |
|   | 5  | 1  | 32     | 0.36   | 110.00 |
|   | 5  | 16 | 15     | 0.47   | 112.00 |
|   | 5  | 16 | 16     | 0.47   | 113.36 |
|   | 5  | 16 | 32     | 0.58   | 100.00 |
|   | 5  | 20 | 8      | 0.36   | 98.90  |
|   | 5  | 20 | 9      | 0.54   | 98.90  |
|   | 5  | 20 | 22     | 0.50   | 115.10 |
|   | 5  | 20 | 31     | 0.38   | 112.20 |
|   | 5  | 22 | 15     | 0.36   | 107.90 |
|   | 5  | 22 | 20     | 0.49   | 114.10 |
|   | 5  | 22 | 32     | 0.55   | 118.00 |
|   | 7  | 3  | 16     | 0.86   | 110.60 |
|   | 8  | 20 | 22     | 0.56   | 117.30 |
|   | 8  | 20 | 31     | 0.56   | 115.00 |
|   | 9  | 20 | 22     | 0.74   | 118.70 |
|   | 9  | 20 | 31     | 0.73   | 116.50 |
|   | 12 | 20 | 13     | 1.03   | 111.11 |
|   | 12 | 20 | 22     | 0.35   | 115.30 |
|   | 12 | 20 | 31     | 0.35   | 114.70 |
|   | 13 | 20 | 22     | 0.36   | 117.70 |
|   | 13 | 20 | 31     | 0.36   | 110.50 |
|   | 14 | 9  | 20     | 0.53   | 137.90 |
|   | 15 | 1  | 16     | 1.09   | 117.00 |
|   | 15 | 16 | 16     | 1.07   | 131.10 |
|   | 15 | 22 | 20     | 0.39   | 116.00 |
|   | 15 | 22 | 32     | 0.62   | 111.00 |
|   | 16 | 1  | 3      | 0.67   | 112.70 |
|   | 16 | 1  | 32     | 1.04   | 110.60 |
|   | 16 | 3  | 30     | 1.17   | 116.50 |
|   | 16 | 15 | 22     | 1.04   | 97.60  |
|   | 16 | 16 | 32     | 1.16   | 120.00 |
|   | 16 | 32 | 22     | 0.97   | 126.10 |
|   | 16 | 32 | 31     | 0.41   | 134.00 |
| 4 | 20 | 22 | 32     | 1.17   | 88.30  |
| 4 | 20 | 31 | 32     | 0.94   | 90.30  |
|   | 20 | 31 | 28     | 0.69   | 138.00 |
| 4 | 22 | 20 | 31     | 1.24   | 85.80  |
| 4 | 22 | 32 | 31     | 1.01   | 94.60  |
|   | 30 | 3  | 30     | 0.85   | 126.00 |
|   | 32 | 31 | 28     | 0.67   | 132.00 |
|   |    | 3  | 16     | 0.80   |        |
|   |    | 3  | 30     | 0.80   |        |
|   |    | 9  | 20     | 0.05   |        |
|   |    | 20 | 31     | 0.80   |        |
|   |    | 31 | 32     | 0.80   |        |

A second necessary requirement for the use of MMP2(85) is the provision of the initial set of cartesian coordinates. For small molecules, such as penicillins and cephalosporins, the coordinates of an experimental crystal structure can be used. Minimization with the appropriate parameters then leads to a calculated structure that reproduces the experimental structure. From this structure it is possible to proceed to other conformations and to the global minimum of the molecule by a series of dihedral drives around each of the dihedral angles of the molecule. This is an option available in MMP2(85), and it works well. However, such a strategy is impractical for the analysis of a peptide because of the very large number of dihedral angles that would have to be examined for any such molecule which contains more than two or three amino acid residues.

Therefore, the computer programme ECEPP (Empirical Conformational Energy Program for Peptides), which is available from QCPE, was modified to allow a random number generator to calculate the one-point energies of 200,000 initial structures containing permutations of the most probable backbone and dihedral angles. The fifty lowest energy structures identified in this manner are read out, minimized using a quadratic minimization procedure, and then converted to the MMP2(85) format for final minimization by the Newton-Raphson procedure. The objective of this initial search is to identify, for example, Damascus as a closer starting point than Tokyo in a search for the Dead Sea. This strategy has been tested extensively, works well, and has been applied to the treatment of a PBP, as described below.

With these procedures in place, an initial series of nine penicillins (1a–1i) was examined. Of these nine compounds, 1a–1d are highly active antibiotics widely used in medicine (ampicillin, syncillin, penicillin G, penicillin V), 1e–1f are significantly less active, and 1g–1i are biologically inactive. The conformational analyses of these compounds revealed that antibacterial activity is associated specifically with a three dimensional structure in which the carboxyl group and side chain N—H project onto the convex face, and engage in hydrogen bonding lock and key interactions with the receptor, i.e., the PBP.

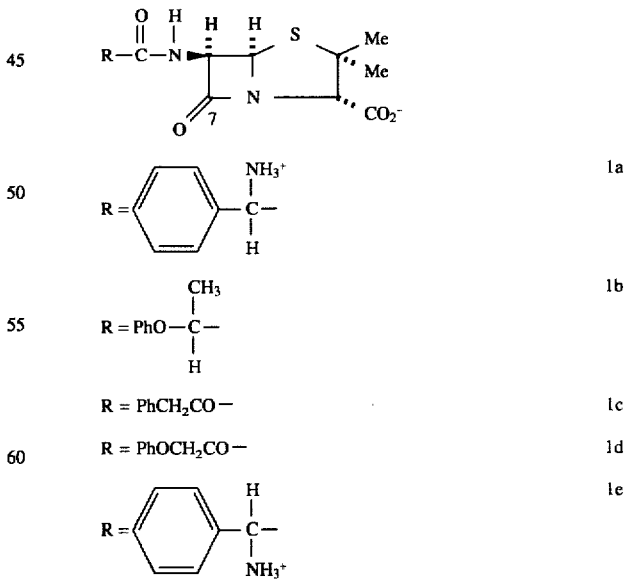

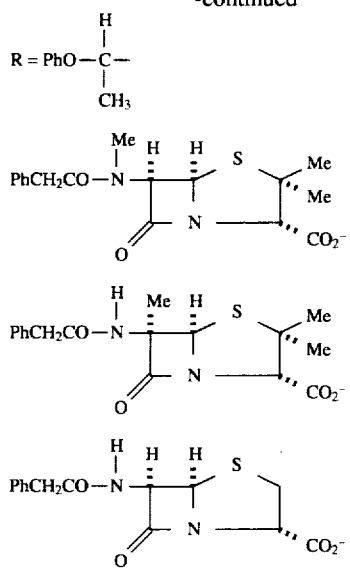

R = PhO—CH(CH₃)—

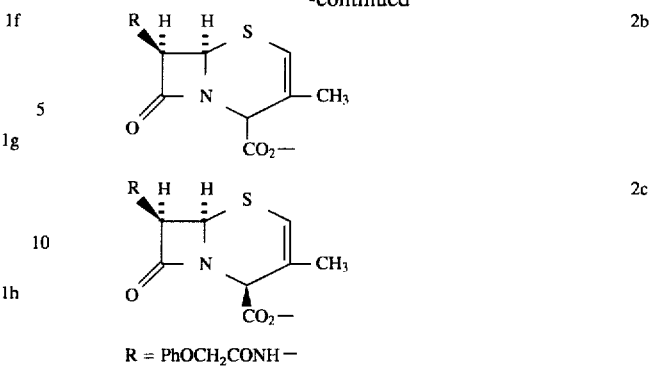

R = PhOCH₂CONH—

Next a conformational analysis was performed on the cephalosporins 2a–2c. Each of these has the phenoxyacetyl side chain, and can therefore be compared to penicillin V (1d). The $\Delta^3$-isomer 2a is biologically active, but undergoes a facile equilibration with the $\Delta^2$-isomer 2b, which is biologically inactive. The reason for the lack of activity of 2b has not previously been established, but it has been suggested that the 4-epi-$\Delta^2$-isomer 2c would exhibit a better fit to the PBP receptor, and possess antibacterial activity. However, such compounds are also inactive. The reason for this lack of activity is, therefore, also unknown.

Each of 2a–2c, like the penicillins 1a–1d, is found to prefer a conformation in which the side chain N—H occupies the convex face of the molecule. As with the penicillins, it can thus be postulated that lock and key interactions with the receptor involve primary binding by the carboxyl group and this side chain N—H.

The active site serine D-alanyl carboxypeptidase-transpeptidase of Streptomyces R61 has been crystallized with incorporation of β-lactam compounds, and the crystal structure has been partially solved. The pH-dependence of the same enzyme has also been examined. Both kinds of studies suggest that the carboxyl group of a penicillin is closely associated with the protonated terminal amino group of the lysine residue of X-X-Lys. The crystal structure confirms that, in the complex, the β-lactam ring of penicillin is in close proximity to the active site serine; the pH-dependence study rules out involvement of a histidine residue in the chemical process, in contrast to the behaviour of chymotrypsin and related serine proteases. This result means that the serine O—H participates in the chemical reaction with the substrate.

These observations suggest that a valid model of the active site of a PBP can be obtained in terms of the amino acids that surround the unique serine residue, i.e., in this case, Val-Gly-Ser-Val-Thr-Lys. Accordingly, the peptide Ac-Val-Gly-Ser-Val-Thr-Lys-NH-CH₃ was subjected to an ECEPP search of 200,000 initial structures, followed by MMP2(85) refinement of 50 low energy structures identified in this search. One low energy structure having the lysine and serine side chains in proximity was found. This structure is characterized by the set of dihedral angles summarized in Table 4, and is shown as FIG. 1.

TABLE 4

Dihedral angles of the model of the active site of the PBP of Streptomyces R61

| Residue | $\phi$ | $\psi$ | $\omega$ | $\chi^1$ | $\chi^2$ | $\chi^3$ | $\chi^4$ | $\chi^5$ |
|---|---|---|---|---|---|---|---|---|
| Ac | | | 180 | | | | | |
| Val | −72 | 121 | 180 | −60 | 178 | 180 | | |
| Gly | 160 | −179 | 178 | | | | | |
| Ser | 79 | −62 | −177 | −55 | 62 | | | |
| Val | 72 | −86 | 177 | −52 | 180 | 180 | | |
| Thr | −71 | 152 | 176 | −172 | 176 | −179 | | |
| Lys | −69 | −47 | 179 | −179 | 62 | 176 | 180 | 180 |

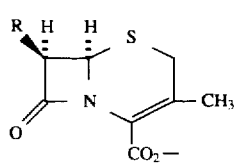

2a

The structure of FIG. 1 has several features of interest. The convex face is mainly hydrophobic, and the concave face, which includes the serine and lysine side chains, is mainly hydrophilic. The concave face also contains the amide oxygen of the N-terminal acetyl group. These three sites are noted on FIG. 1 as S (serine), L (lysine) and A (acetyl). The existence of a lock and key relationship between the concave face of FIG. 1 and the previously determined convex face of penicillin and cephalosporin now seems clear. In terms of such a relationship, contact is required between the carboxyl group of the antibiotic and the terminal amino group of lysine, and also between the side chain N—H of the antibiotic and the acetyl oxygen.

The construction of a supermolecule in which the receptor is docked to a substrate through $NH_3^+ \ldots {}^-O_2C$ and N—H $\ldots$ O=C hydrogen bonds is, therefore, desirable. To obtain the structure and energy of such a supermolecule using MMP2(85), it is necessary to devise a procedure for the generation of a starting set of cartesian coordinates.

A computer programme has been written based on the following approach to the problem. Let A refer to a receptor molecule containing $N_1$ atoms, and B a substrate molecule containing $N_2$ atoms, which is to be docked to A. We assume that the geometries of A and B are known in Cartesian or internal coordinates, and that transformation between the two types of coordinate systems is possible. We thus begin with $(3N_1-6)$ and $(3N_2-6)$ predetermined internal coordinates. To describe the geometry of the supermolecule containing $(N_1+N_2)$ atoms requires $3(N_1+N_2)-6$ internal coordinates, i.e., six new internal coordinates must be determined and minimized. These comprise, typically, one bond length, two bond angles, and three dihedral angles, and they may be termed "intermolecular" internal coordinates.

To use the computer programme, summarized in Table 5, one of the desired hydrogen bonding interactions is selected, and its distance set at 1.7–2.5 Å, a typical intermolecular hydrogen bonding distance. Initial values are then given to the five remaining variables, and the energy is minimized, with the second hydrogen bond distance as a probe. The geometry of the resulting supermolecule, now expressed in Cartesian coordinates, is considered appropriate for MMP2(85) minimization when the second hydrogen bond distance is 1.7–2.5 Å.

TABLE 5

PROGRAMME FOR DOCKING OF TWO MOLECULES

```
                                                              SUP00010
                                                              SUP00020
                                                              SUP00030
PARAMETER (NT = 150)                                          SUP00040
PARAMETER (NG = 300)                                          SUP00050
CHARACTER*2 ASYM, TITLE                                       SUP00060
INTEGER TYPEA, TYPEB, TYP                                     SUP00070
COMMON/COOD/COORD(3, NG), CHARGE(NG)                          SUP00080
COMMON/TYPE/TYPEA(NT), TYPEB(NT), TYP(NG)                     SUP00090
COMMON/SYMM/ASYM(NG), TITLE(40)                               SUP00100
COMMON/PARAM/VEP(NG), VRA(NG)                                 SUP00110
COMMON/CORD/XA(NT), YA(NT), ZA(NT), XB(NT), YB(NT), ZB(NT)    SUP00120
COMMON/FINAL/TXB(NT), TYB(NT), TZB(NT), CA(NT), CB(NT)        SUP00130
COMMON/INFO/NA, NB, IP1, IP2, IP3, IP4, R1, R2, CIP2, CIP4, JCON  SUP00140
COMMON/PATH/MYWAY                                             SUP00150
DIMENSION X(5), E(5)                                          SUP00160
DATA E/5*0.01/                                                SUP00170
READ(8, 10) TITLE                                             SUP00180
FORMAT(40A2)                                                  SUP00190
READ(8, *) IP1, IP2, IP3, IP4, MYWAY, R1, R2, SC              SUP00200
MYWAY = 1: DISTANCE                                           SUP00210
MYWAY = 2: ENERGY                                             SUP00220
SC = SPECIAL CHARGE                                           SUP00230
CALL COMBIN(NA, NB)                                           SUP00240
READ(8, *) THETA, PI, XROT, YROT, ZROT, SCALE, JCON, EE1      SUP00250
E(1) = EE1                                                    SUP00260
E(2) = EE1                                                    SUP00270
E(3) = EE1                                                    SUP00280
E(4) = EE1                                                    SUP00290
E(5) = EE1                                                    SUP00300
READ(5, *) (E(I), I = 1, 5)                                   SUP00310
SPECIAL CHARGE FOR IP2 AND IP4                                SUP00320
CIP2 = SC                                                     SUP00330
CIP4 = -SC                                                    SUP00340
IPRINT = 1                                                    SUP00350
ICON = 1                                                      SUP00360
CONVERT DEGREE TO RADIAN                                      SUP00370
DEGREE = 57.29577951D0                                        SUP00380
                                                              SUP00390
X(1) = THETA/DEGREE                                           SUP00400
X(2) = PI/DEGREE                                              SUP00410
X(3) = XROT/DEGREE                                            SUP00420
X(4) = YROT/DEGREE                                            SUP00430
X(5) = ZROT/DEGREE                                            SUP00440
NVAR = 5                                                      SUP00450
                                                              SUP00460
READ COORDINATE WITH MM FORMAT                                SUP00470
READ(4, 20) (XA(I), YA(I), ZA(I), TYPEA(I), I = 1, NA)        SUP00480
FORMAT(2(3F10.5, I5, 5X))                                     SUP00490
READ(5, 20) (XB(I), YB(I), ZB(I), TYPEB(I), I = 1, NB)        SUP00500
CALL SYMBOL                                                   SUP00510
CALL IWRITE                                                   SUP00520
CALL PARM                                                     SUP00530
CALL CHARG                                                    SUP00540
                                                              SUP00550
WRITE(6, 22) (CHARGE (I), I = 1, 12)
```

TABLE 5-continued

PROGRAMME FOR DOCKING OF TWO MOLECULES

| | |
|---|---|
| FORMAT(3X, 6F10.4) | SUP00560 |
| | SUP00570 |
| CALL OPTIM(X, NVAR, SCALE, IPRINT, ICON, E) | SUP00580 |
| | SUP00590 |
| CONVERT RADIAN TO DEGREE | SUP00600 |
| DO 30 J = 1, 5 | SUP00610 |
| X(J) = X(J)*DEGREE | SUP00620 |
| WRITE(6, 35) X | SUP00630 |
| FORMAT(4X, 'OPTIMIZED THETA-PI-X-Y-Z ANGLES', //, 3X, 5(F10.5, 3X)) | SUP00640 |
| WRITE BOND DISTANCE BETWEEN IP2 AND IP4 | SUP00650 |
| X1 = XA(IP2) | SUP00660 |
| Y1 = YA(IP2) | SUP00670 |
| Z1 = ZA(IP2) | SUP00680 |
| X2 = TXB(IP4) | SUP00690 |
| Y2 = TYB(IP4) | SUP00700 |
| Z2 = TZB(IP4) | SUP00710 |
| R12 = DIST(X1, Y1, Z1, X2, Y2, Z2) | SUP00720 |
| WRITE(6, 40) IP2, IP4, R12 | SUP00730 |
| DO 50 K = 1, NA | SUP00740 |
| COORD(1, K) = XA(K) | SUP00750 |
| COORD(2, K) = YA(K) | SUP00760 |
| COORD(3, K) = ZA(K) | SUP00770 |
| CONTINUE | SUP00780 |
| NTOT = NA + NB | SUP00790 |
| DO 60 KK = 1, NB | SUP00800 |
| COORD(1, NA + KK) = TXB(KK) | SUP00810 |
| COORD(2, NA + KK) = TYB(KK) | SUP00820 |
| COORD(3, NA + KK) = TZB(KK) | SUP00830 |
| CONTINUE | SUP00840 |
| FORMAT(//, 'BOND LENGTH BETWEEN ',I3,' OF A AND ',I4,' OF B IS' | SUP00850 |
| 1, F10.5, 'ANGSTROM', //) | SUP00860 |
| | SUP00870 |
| CALL CHEMG(NTOT) | SUP00880 |
| CALL MMDATA | SUP00890 |
| WRITE FINAL CARTESIAN COORDINATE FOR CHEMGRAF | SUP00900 |
| WRITE(6, '(//10X, "FINAL CARTESIAN COORDINATES",/)'0 | SUP00910 |
| WRITE(6, '(4X, "NO.", 7X, "ATOM", 9X, "X", | SUP00920 |
| 1 9X, "Y", 9X, "Z",/)') | SUP00930 |
| WRITE(6, '(I6, 8X, A2, 4X, 3F10.5)') | SUP00940 |
| 1 (I, ASYM(I), (COORD(J, I), J = 1, 3), I = 1, NTOT) | SUP00950 |
| | SUP00960 |
| STOP | SUP00970 |
| END | SUP00980 |
| ROUTINE FOR OUTPUT IF INITIAL COORDINATES | SUP00990 |
| SUBROUTINE IWRITE | SUP01000 |
| PARAMETER (NT = 150) | SUP01010 |
| PARAMETER (NG = 300) | SUP01020 |
| CHARACTER*2 ASYM TITLE | SUP01030 |
| INTEGER TYPEA, TYPEB TYP | SUP01040 |
| COMMON/COOD/ COORD(3, NG), CHARGE(NG) | SUP01050 |
| COMMON/TYPE/TYPEA(NT), TYPEB(NT), TYP(NG) | SUP01060 |
| COMMON/SYMM/ASYM(NG), TITLE(40) | SUP01070 |
| COMMON/CORD/XA(NT), YA(NT), ZA(NT), XB(NT), YB(NT), ZB(NT) | SUP01080 |
| COMMON/FINAL/TXB(NT), TYB(NT), TZB(NT), CA(NT), CB(NT) | SUP01090 |
| COMMONINFO/NA, NB, IP1, IP2, IP3, IP4, R1, R2, CIP2, CIP4, JCON | SUP01100 |
| WRITE(6, 15) TITLE | SUP01110 |
| FORMAT(1H1, /////, | SUP01120 |
| 1 10X, '*****************************************',/, | SUP01130 |
| 2 10X, 'COORDINATES OF SUPERMOLECULE',/, | SUP01140 |
| 3 15X, 40A2,/, | SUP01150 |
| 4 10X, '*****************************************') | SUP01160 |
| WRITE CARTESIAN COORDINATE | SUP01170 |
| WRITE(6, '(//10X, "INITIAL CARTESIAN COORDINATES OF A ",/)') | SUP01180 |
| WRITE(6, '(4X, "NO.", 7X, "ATOM", 9X, "X", | SUP01190 |
| 1 9X, "Y", 9X, "Z",/)') | SUP01200 |
| WRITE(6, '(I6, 8X, A2, 4X, 3F10.5)') | SUP01210 |
| 1 (I, ASYM(I), XA(I), YA(I), ZA(I), I = 1, NA) | SUP01220 |
| | SUP01230 |
| WRITE(6, '(////10X, "INITIAL CARTESIAN COORDINATES OF B ",/)') | SUP01240 |
| WRITE(6, '(4X, "NO.", 7X, "ATOM", 9X, "X", | SUP01250 |
| 1 9X, "Y", 9X, "2",/)') | SUP01260 |
| WRITE(6, '(I6, 8X, A2, 4X, 3F10.5)') | SUP01270 |
| 1 (I, ASYM(NA + I), XB(I), YB(I), ZB(I), I = 1, NB) | SUP01280 |
| WRITE(6, '(//)') | SUP01290 |
| RETURN | SUP01300 |
| END | SUP01310 |
| SUBROUTINE OPTIM (X, N, ESCALE, IPRINT, ICON, E) | SUP01320 |

TABLE 5-continued
PROGRAMME FOR DOCKING OF TWO MOLECULES

```
PARAMETER (NT = 150)                                    SUP01330
DIMENSION W(1000), X(5), E(5)                           SUP01340
MAXIT = 100                                             SUP01350
DDMAG = 0.1*ESCALE                                      SUP01360
SCER = 0.05/ESCALE                                      SUP01370
JJ = N*N + N                                            SUP01380
JJJ = JJ + N                                            SUP01390
K = N + 1                                               SUP01400
NFCC = 1                                                SUP01410
IND = 1                                                 SUP01420
INN = 1                                                 SUP01430
DO 1 I = 1, N                                           SUP01440
DO 2 J = 1, N                                           SUP01450
W(K) = 0.                                               SUP01460
IF(I - J)4, 3, 4                                        SUP01470
W(K) = ABS(E(I))                                        SUP01480
W(I) = ESCALE                                           SUP01490
K = K + 1                                               SUP01500
CONTINUE                                                SUP01510
CONTINUE                                                SUP01520
ITERC = 1                                               SUP01530
ISCRAD = 2                                              SUP01540
CALL CALCFX(N, X, F, EVV, ECO, EIDS)                    SUP01550
FKEEP = ABS(F) + ABS(F)                                 SUP01560
ITONE = 1                                               SUP01570
FP = F                                                  SUP01580
SUM = 0.                                                SUP01590
IXP = JJ                                                SUP01600
DO 6 I = 1, N                                           SUP01610
IXP = IXP + 1                                           SUP01620
W(IXP) = X(I)                                           SUP01630
CONTINUE                                                SUP01640
IDIRN = N + 1                                           SUP01650
ILINE = 1                                               SUP01660
DMAX = W(ILINE)                                         SUP01670
DACC = DMAX*SCER                                        SUP01680
DMAG = MIN (DDMAG, 0.1*DMAX)                            SUP01690
DMAG = MAX(DMAG, 20.*DACC)                              SUP01700
DDMAX = 10.*DMAG                                        SUP01710
GO TO (70, 70, 71), ITONE                               SUP01720
DL = 0.                                                 SUP01730
D = DMAG                                                SUP01740
FPREV = F                                               SUP01750
IS = 5                                                  SUP01760
FA = F                                                  SUP01770
DA = DL                                                 SUP01780
DD = D - DL                                             SUP01790
DL = D                                                  SUP01800
K = IDIRN                                               SUP01810
DO 9 I = 1, N                                           SUP01820
X(I) = X(I) + DD*W(K)                                   SUP01830
K = K + 1                                               SUP01840
CONTINUE                                                SUP01850
CALL CALCFX(N, X, F, EVV, ECO, EDIS)                    SUP01860
NFCC = NFCC + 1                                         SUP01870
GO TO (10, 11, 12, 13, 14, 96), IS                      SUP01880
IF(F - FA)15, 16, 24                                    SUP01890
IF (ABS(D) - DMAX) 17, 17, 18                           SUP01900
D = D + D                                               SUP01910
GO TO 8                                                 SUP01920
WRITE(6, 19)                                            SUP01930
FORMAT(5X, 44NVA04A MAXIMUM CHANGE DOES NOT ALTER FUNCTION)  SUP01940
GO TO 500                                               SUP01950
FB = F                                                  SUP01960
DB = D                                                  SUP01970
GO TO 21                                                SUP01980
FB = FA                                                 SUP01990
DB = DA                                                 SUP02000
FA = F                                                  SUP02010
DA = D                                                  SUP02020
GO TO (83, 23), ISGRAD                                  SUP02030
D = DB + DB - DA                                        SUP02040
IS = 1                                                  SUP02050
GO TO 8                                                 SUP02060
D = 0.5*(DA + DB - (FA - FB)/(DA - DB))                 SUP02070
IS = 4                                                  SUP02080
IF((DA - D)*(D - DB))25, 8, 8                           SUP02090
```

TABLE 5-continued

PROGRAMME FOR DOCKING OF TWO MOLECULES

| | |
|---|---|
| IS = 1 | SUP02100 |
| IF(ABS(D − DB) − DDMAX)8, 8, 26 | SUP02110 |
| D = DB + SIGN(DDMAX, DB − DA) | SUP02120 |
| IS = 1 | SUP02130 |
| DDMAX = DDMAX + DDMAX | SUP02140 |
| DDMAG = DDMAG + DDMAG | SUP02150 |
| IF(DDMAX − DMAX)8, 8, 27 | SUP02160 |
| DDMAX = DMAX | SUP02170 |
| GO TO 8 | SUP02180 |
| IF(F − FA)28, 23, 23 | SUP02190 |
| FC = FB | SUP02200 |
| DC = DB | SUP02210 |
| FB = F | SUP02220 |
| DB = D | SUP02230 |
| GO TO 30 | SUP02240 |
| IF(F − FB)28, 28, 31 | SUP02250 |
| FA = F | SUP02260 |
| DA = D | SUP02270 |
| GO TO 30 | SUP02280 |
| IF(F − FB)32, 10, 10 | SUP02290 |
| FA = FB | SUP02300 |
| DA = DB | SUP02310 |
| GO TO 29 | SUP02320 |
| DL = 1. | SUP02330 |
| DDMAX = 5. | SUP02340 |
| FA = FP | SUP02350 |
| DA = −1. | SUP02360 |
| FB = FHOLD | SUP02370 |
| DB = 0. | SUP02380 |
| D = 1. | SUP02390 |
| FC = F | SUP02400 |
| DC = D | SUP02410 |
| A = (DB − DC)*(FA − FC) | SUP02420 |
| B = (DC − DA)*(FB − FC) | SUP02430 |
| IF((A*B)*(DA − DC))33, 33, 34 | SUP02440 |
| FA = FB | SUP02450 |
| DA = DB | SUP02460 |
| FB = FC | SUP02470 |
| DB = DC | SUP02480 |
| GO TO 26 | SUP02490 |
| D = 0.5*(A*(DB + DC) + B*(DA + DC))/(A + B) | SUP02500 |
| DI = DB | SUP02510 |
| FI = FB | SUP02520 |
| IF(FB−FC)44, 44, 43 | SUP02530 |
| DI = DC | SUP02540 |
| FI = FC | SUP02550 |
| GO TO (86, 86, 85), ITONE | SUP02560 |
| ITONE = 2 | SUP02570 |
| GO TO 45 | SUP02580 |
| IF (ABS(D − DI) − DACC) 41, 41, 93 | SUP02590 |
| IF (ABS (D − DI) − 0.03*ABS(D)) 41, 41, 45 | SUP02600 |
| IF (DA − DC)*(DC − D)) 47, 46, 46 | SUP02610 |
| FA = FB | SUP02620 |
| DA = DB | SUP02630 |
| FB = FC | SUP02640 |
| DB = DC | SUP02650 |
| GO TO 25 | SUP02660 |
| IS = 2 | SUP02670 |
| IF ((DB − D)*(D − DC)) 48, 8, 8 | SUP02680 |
| IS = 3 | SUP02690 |
| GO TO 8 | SUP02700 |
| F = FI | SUP02710 |
| D = DI − DL | SUP02720 |
| DD = SQRT((DC − DB)*(DC − DA)*(DA − DB)/(A + B)) | SUP02730 |
| DO 49 I = 1, N | SUP02740 |
| X(I) = X(I) + D*W(IDIRN) | SUP02750 |
| W(IDIRN) = DD*W(IDIRN) | SUP02760 |
| IDIRN = IDIRN + 1 | SUP02770 |
| CONTINUE | SUP02780 |
| W(ILINE) = W(ILINE)/DD | SUP02790 |
| ILINE = ILINE + 1 | SUP02800 |
| IF(IPRINT − 1)51, 50, 51 | SUP02810 |
| WRITE(6, 52)ITERC, NFCC, F | SUP02820 |
| WRITE(7, 52)ITERC, NFCC, F | SUP02830 |
| FORMAT (3X, 'ITERATION', I5, I9, 'FUNCTION VALUE = ', F15.8) | SUP02840 |
| WRITE(6, 68) EVV, ECO, EDIS | SUP02850 |
| WRITE(7, 68) EVV, ECO, EDIS | SUP02860 |

TABLE 5-continued
PROGRAMME FOR DOCKING OF TWO MOLECULES

```
FORMAT(3X, 'REP. = ', F12.5,' ATT. = , 'F12.5,' R = ', F10.4)              SUP02870
GO TO(51, 53), IPRINT                                                       SUP02880
GO TO (55, 38), ITONE                                                       SUP02890
IF (FPREV - F - SUM) 94, 95, 95                                             SUP02900
SUM = FPREV - F                                                             SUP02910
JIL = ILINE                                                                 SUP02920
IF (IDIRN - JJ) 7, 7, 84                                                    SUP02930
GO TO (92, 72), IND                                                         SUP02940
FHOLD = F                                                                   SUP02950
IS = 6                                                                      SUP02960
IXP = JJ                                                                    SUP02970
DO 59 I = 1, N                                                              SUP02980
IXP = IXP + 1                                                               SUP02990
W(IXP) = X(I) - W(IXP)                                                      SUP03000
CONTINUE                                                                    SUP03010
DD = 1.                                                                     SUP03020
GO TO 58                                                                    SUP03030
GO TO (112, 87), IND                                                        SUP03040
IF (FP - F) 37, 91, 91                                                      SUP03050
D = 2.*(FP*F - 2.*FHOLD)/(FP - F)**2                                        SUP03060
IF (D*(FP - FHOLD - SUM)**2 - SUM) 87, 37, 37                               SUP03070
J = JIL*N + 1                                                               SUP03080
IF (J - JJ) 60, 60, 61                                                      SUP03090
DO 62 I = J, JJ                                                             SUP03100
K = I - N                                                                   SUP03110
W(K) = W(I)                                                                 SUP03120
CONTINUE                                                                    SUP03130
DO 97 I = JIL, N                                                            SUP03140
W(I - 1) = W(I)                                                             SUP03150
CONTINUE                                                                    SUP03160
IDIRN = IDIRN - N                                                           SUP03170
ITONE = 3                                                                   SUP03180
K = IDIRN                                                                   SUP03190
IXP = JJ                                                                    SUP03200
AAA = 0.                                                                    SUP03210
DO 65 I = 1, N                                                              SUP03220
IXP = IXP + 1                                                               SUP03230
W(K) = W(IXP)                                                               SUP03240
IF (AAA - ABE(W(K)/E(I))) 66, 67, 67                                        SUP03250
AAA = ABS(W(K)/E(I))                                                        SUP03260
K = K - 1                                                                   SUP03270
CONTINUE                                                                    SUP03280
DDMAG = 1.                                                                  SUP03290
W(N) = ESCALE/AAA                                                           SUP03300
ILINE = N                                                                   SUP03310
GO TO 7                                                                     SUP03320
IXP = JJ                                                                    SUP03330
AAA = 0.                                                                    SUP03340
F = FHOLD                                                                   SUP03350
DO 99 I = 1, N                                                              SUP03360
IXP = IXP + 1                                                               SUP03370
X(I) = X(I) - W(IXP)                                                        SUP03380
IF (AAA*ABS(E(I)) - ABS(W(IXP))) 98, 99, 99                                 SUP03390
AAA = ABS(W(IXP)/E(I))                                                      SUP03400
CONTINUE                                                                    SUP03410
GO TO 72                                                                    SUP03420
AAA = AAA*(1. + DI)                                                         SUP03430
GO TO (72, 106), IND                                                        SUP03440
IF (IPRINT - 2) 53, 50, 50                                                  SUP03450
GO TO (109, 88), IND                                                        SUP03460
IF (AAA - 0.1) 89, 89, 76                                                   SUP03470
GO TO (20, 116), ICON                                                       SUP03480
IND = 2                                                                     SUP03490
GO TO (100, 101), INN                                                       SUP03500
INN = 2                                                                     SUP03510
K = JJJ                                                                     SUP03520
DO 102 I = 1, N                                                             SUP03530
K = K + 1                                                                   SUP03540
W(K) = X(I)                                                                 SUP03550
X(I) = X(I) + 10.*E(I)                                                      SUP03560
CONTINUE                                                                    SUP03570
FKEEP = F                                                                   SUP03580
CALL CALCFX(N, X, F, EVV, ECO, EDIS)                                        SUP03590
NFCC = NFCC + 1                                                             SUP03600
DDMAG = 0                                                                   SUP03610
GO TO 108                                                                   SUP03620
IF (F - FP) 35, 78, 78                                                      SUP03630
```

TABLE 5-continued
PROGRAMME FOR DOCKING OF TWO MOLECULES

```
WRITE(6, 80)                                                    SUP03640
FORMAT (5X, 37HVA04A ACCURACY LIMITED BY ERRORS IN F)           SUP03650
GO TO 500                                                       SUP03660
IND = 1                                                         SUP03670
DDMAC = 0.4*SQRT(FP − F)                                        SUP03680
IF(DDMAG.GE.1.0EG0) DDMAG = 1.0E60                              SUP03690
ISCRAD = 1                                                      SUP03700
ITERC = ITERC + 1                                               SUP03710
IF (ITERC − MAXIT) 5, 5, 81                                     SUP03720
WRITE(6, 82)MAXIT                                               SUP03730
FORMAT(15, 30H ITERATIONS COMPLETED BY VA04A)                   SUP03740
IF (F − FKEEP) 500, 500, 110                                    SUP03750
F = FKEEP                                                       SUP03760
DO 111 I = 1, N                                                 SUP03770
JJJ = JJJ4 − 1                                                  SUP03780
X(I) = W(JJJ)                                                   SUP03790
CONTINUE                                                        SUP03800
GO TO 20                                                        SUP03810
JIL = 1                                                         SUP03820
FP = FKEEP                                                      SUP03830
IF (F − FKEEP) 105, 78, 104                                     SUP03840
JIL = 2                                                         SUP03850
FP = F                                                          SUP03860
F = FKEEP                                                       SUP03870
IXP = JJ                                                        SUP03890
DO 113 I = 1, N                                                 SUP03890
IXP = IXP + 1                                                   SUP03900
K = IXP + N                                                     SUP03910
GO TO (114, 115), JIL                                           SUP03920
W(IXP) = W(K)                                                   SUP03930
GO TO 113                                                       SUP03940
W(IXP) = X(I)                                                   SUP03550
X(I) = W(K)                                                     SUP03960
CONTINUE                                                        SUP03970
JIL = 2                                                         SUP03980
GO TO 92                                                        SUP03990
IF (AAA − 0.1) 20, 20, 107                                      SUP04000
WRITE(6, 200)                                                   SUP04010
WRITE(6, 201)                                                   SUP04020
WRITE(7, 201)                                                   SUP04030
FORMAT(5X, 'THE FUNCTION VALUE HAS BEEN MINIMIZED.')            SUP04040
WRITE(6, 200)                                                   SUP04050
FORMAT(/1X, '**********************************************'/)  SUP04060
RETURN                                                          SUP04070
INN = 1                                                         SUP04080
GO TO 35                                                        SUP04090
END                                                             SUP04100
                                                                SUP04110
SUBROUTINE PARM                                                 SUP04120
PARAMETER (NT = 150)                                            SUP04130
PARAMETER (NG = 300)                                            SUP04140
CHARACTER*2 ASYM, TITLE                                         SUP04150
INTEGER TYPEA, TYPEB TYP                                        SUP04160
COMMON/PARAM/VEP(NG), VRA(NG)                                   SUP04170
COMMON/rNFO/NA, NB, IP1, IP2, IP3, IP4, R1, R2, CIP2, CIP4, JCON SUP04180
COMMON/TYPE/TYPEA(NT), TYPEB(NT), TYP(NG)                       SUP04190
DIMENSION VEPS(60), VRAD(60)                                    SUP04200
                                                                SUP04210
DATA VRAD/                                                      SUP04220
1 1.900, 1.940, 1.940, 1.940, 1.500, 1.740, 1.740, 1.820, 1.820, SUP04230
2 −1.0, 1.780, 1.740, 1.900, 0.930, 2.110, 1.920, −1.0, −1.0,   SUP04240
3 1.820, 1.920, 1.200, 1.920, 1.325, 0.900, 1.25, 1.820, 1.94,  SUP04250
4 1.740, 1.90, 1.780, 1.92, 1.82, −1.0 , −1.0, −1.0, −1.0,      SUP04260
5 −1.0, −1.0, −1.0, −1.0 , −1.0, −1.0, 17* − 1.0/               SUP04270
DATA VEPS/                                                      SUP04280
1 0.044, 0.044, 0.044, 0.044, 0.047, 0.050, 0.066, 0.055, 0.055, SUP04290
2 −1.0, 0.066, 0.050, 0.030, 0.017, 0.202, 0.044, −1.0, −1.0,   SUP04300
3 0.055, 0.044, 0.036, 0.044, 0.034, 0.015, 0.036, 0.055, 0.044, SUP04310
4 0.066, 0.044, 0.066, 0.044, 0.055, −1.0, −1.0, −1.0 , −1.0,   SUP04320
5 −1.0, −1.0, −1.0, −1.0, −1.0, −1.0, 17* − 1.0/                SUP04330
IF(JCON.GT.0) THEN                                              SUP04340
DO 10 J = 1, JCON                                               SUP04350
READ(5, *) ITYPE, EPS, RAD                                      SUP04360
VEPS(ITYPE) = EPS                                               SUP04370
VRAD(ITYPE) = RAD                                               SUP04380
CONTINUE                                                        SUP04390
ENDIF                                                           SUP04400
```

TABLE 5-continued
PROGRAMME FOR DOCKING OF TWO MOLECULES

```
DO 20 I = 1, NA                                                  SUP04410
VEP(I) = VEPS(TYPEA(I))                                          SUP04420
IF(VEP(I).LE - 0.0) THEN                                         SUP04430
WRITE(7, 25) TYPEA(I)                                            SUP04440
ENDIF                                                            SUP04450
VRA(I) = VRAD(TYPEA(I))                                          SUP04460
TF(VRA(I).LE.0.0) THEN                                           SUP04470
WRITE(7, 25) TYPEA(L)                                            SUP04480
FORMAT(4X, 'CHECK YOUR VAN DER WAAL DATA OF ATOM TYPE', I4)      SUP04490
ENDIF                                                            SUP04500
CONTINUE                                                         SUP04510
                                                                 SUP04520
DO 30 II = 1, NB                                                 SUP04530
VEP(NA + I) = VEPS(TYPEB(I))                                     SUP04540
IF(VEP(NA + I).LE - 0.0) THEN                                    SUP04550
WRITE(7, 25) TYPEB(I)                                            SUP04560
ENNDIF                                                           SUP04570
VRA(NA + I) = VRAD(TYL)EB(I))                                    SUP04580
IF(VRA(NA + I).LE.0.0) THEN                                      SUP04590
WRITE(7, 25) TYPEB(I)                                            SUP04600
ENDIF                                                            SUP04610
CONTINUE                                                         SUP04620
RETURN                                                           SUP04630
END                                                              SUP04640
SUBROUTINE ENERGY(ETOT, EV, ETOT1, EDIS)                         SUP04650
FUNCTION PROGRAM FOR SUPER-MOLECULE                              SUP04660
PARAMETER (NT = 150)                                             SUP04670
PARAMETER (NG = 300)                                             SUP04680
CHARACTER*2 ASYM, TITLE                                          SUP04690
INTEGER TYPEA, TYPEB, TYP                                        SUP04700
COMMON/COOD/COORD(3, NG), CHARGE(NG)                             SUP04710
COMMON/TYPE/TYPEA(NT), TYPEB(NT) TYP(NG)                         SUP04720
COMMON/CORD/XA(NT)*YA(NT), ZA(NT), XB(NT), YB(NT), ZB(NT)        SUP04730
COMMON/FINAL/TXB(NT), TYB(NT), TZB(NT), CA(NT), CB(NT)           SUP04740
COMMON/PARAM/VEP(NG), VRA(NG)                                    SUP04750
COMMON/INFO/NA, NB, IP1, IP2, IP3, IP4, R1, R2, CIP2, CIP4, JCON SUP04760
COMMON/PATH/MYWAY                                                SUP04770
CALCULATION OF VAN DER WALLS ENERGY(ONLY 1-5 AND HIGHTER ORDER)  SUP04780
DIELC = 78.5                                                     SUP04790
GO TO (1, 2), MYWAY                                              SUP04800
X1 = XA(IP2)                                                     SUP04810
Y1 = YA(IP2)                                                     SUP04820
Z1 = ZA(IP2)                                                     SUP04830
X2 = TXB(IP4)                                                    SUP04840
Y2 = TYB(IP4)                                                    SUP04850
Z2 = TZB(IP4)                                                    SUP04860
ETOT1 = DIST(X1, Y1, Z1, X2, Y2, Z2)                             SUP04870
ETOT1= ABS(ETOT1 - R2) *500.0                                    SUP04880
IF(MYWAY.EQ.1) THEN                                              SUP04890
ETOT = ETOT1                                                     SUP04900
RETURN                                                           SUP04910
ENDIF                                                            SUP04920
                                                                 SUP04930
EV = 0.0                                                         SUP04940
EC = 0.0                                                         SUP04950
DO 500 I = 1, NA                                                 SUP04960
XI = XA(I)                                                       SUP04970
YI = YA(I)                                                       SUP04980
ZI = ZA(I)                                                       SUP04990
DO 500 K = 1, NB                                                 SUP05000
XK = TXB(K)                                                      SUP05010
YK = TYB(K)                                                      SUP05020
ZK = TZB(K)                                                      SUP05030
RIK = DIST(XI, YI, ZI, XK, YK, 2K)                               SUP05040
ECOUL = 332.0*CHARGE(I)*CHARGE(NA + K)/(DIELC*RIK)               SUP05050
VEPI = VEP(I)                                                    SUP05060
VEPK = VEP(NA + K)                                               SUP05070
VRAI = VRA(I)                                                    SUP05080
VRAK = VRA(NA + K)                                               SUP05090
EPS = SQRT(VEPI*VEPK)                                            SUP05100
RV = VRAI + VRAK                                                 SUP05110
P = RV/RIK                                                       SUP05120
IF(P.GT.3.31) GO TO 30                                           SUP05130
IF(P.LT.0.072) THEN                                              SUP05140
E = EPS*(-2.25*p**6)                                             SUP05150
GO TO 35                                                         SUP05160
ENDIF                                                            SUP05170
```

TABLE 5-continued

PROGRAMME FOR DOCKING OF TWO MOLECULES

```
E = EPS*(290000.0*EXP(-1.2.5/P) - 2.25*P**G)              SUP05180
GO TO 40                                                   SUP05190
E = EPS*33G.176*p*p                                        SUP05200
CONTINUE                                                   SUP05210
EV = EV + E                                                SUP0520
EC = EC - ECOUL                                            SUP05230
CONTINUE                                                   SUP05240
ETOT = EV + ETOT1 + EC                                     SUP05250
ETOT = FV + ETOT1                                          SUP05260
X1 = XA(IP2)                                               SUP05270
Y1 = YA(IP2)                                               SUP05280
Z1 = ZA(IP2)                                               SUP05290
X2 = TXB(IP4)                                              SUP05300
Y2 = TYB(IP4)                                              SUP05310
Z2 = TZB(IP4)                                              SUP05320
EDIS = DIST(X1, Y1, Z1, X2, Y2, Z2)                        SUP05330
RETURN                                                     SUP05340
END                                                        SUP05350
FUNCTION DIST                                              SUP05360
FUNCTION DIST(X1, Y1, Z1, X2, Y2, Z2)                      SUP05370
X = X1 - X2                                                SUP05380
Y = Y1 - Y2                                                SUP05390
Z = Z1 - Z2                                                SUP05400
DIST = SQRT(X*X + Y*Y + Z*Z)                               SUP05410
RETURN                                                     SUP05420
END                                                        SUP05430
SUBROUTINE CALCFX(NVAR, X, ETOT, EV, EC, EDIS)             SUP05440
PARAMETER (NT = 150)                                       SUP05450
PARAMETER (NG = 300)                                       SUP05460
COMMON/CORD/XA(NT), YA(NT), ZA(NT), XB(NT), YB(NT), ZB(NT) SUP05470
COMMON/FINAL/TXB(NT), TYB(NT), TZB(NT), CA(NT), CB(NT)     SUP05480
COMMON/INFO/NA, NB, IP1, IP2, IP3, IP4, R1, R2 CIP2, CIP4, JCON SUP05490
DIMENSION X(5), TX(150), TY(150), TZ(150), XROT(9), YROT(9), ZROT(9) SUP05500
DIMENSION CTX(150), CTY(150), CTZ(150)                     SUP05510
CONVERSION OF POLAR COORDINATE TO CARTECIAN COORDINATE OF REF. POINT SUP05520
DX = R1*SIN(X(1))*COS(X(2))                                SUP05530
DY = R1*SIN(X(1))*SIN(X(2))                                SUP05540
DX = R1*COS(X(1))                                          SUP05550
FIXING OF PROBE 2 APART FROM PROBE 1 BY R1 ANG. IN SPACE   SUP05560
PX = XA(IP1) + DX                                          SUP05570
PY = YA(IP1) + DY                                          SUP05580
PZ = ZA(IP1) + DZ                                          SUP05590
CALCULATE DISTANCE VECTORS BETWEEN PROBE P(PX, PY, PZ) AND PROBE 3 SUP05600
DVX = PX - XB(IP3)                                         SUP05610
DVY = PY - YB(IP3)                                         SUP05620
DVZ = PZ - ZB(IP3)                                         SUP05630
PARALLEL MOVEMENT OF B MOLECULE BY (DVX, DVY, DVZ)         SUP05640
DO 10 IM = 1, NB                                           SUP05650
TX(IM) = XB(IM) * DVX                                      SUP05660
TY(IM) = YB(IM) + DVY                                      SUP05670
TZ(IM) = ZB(IM) + DVZ                                      SUP05680
CONTINUE                                                   SUP05690
MOVE TO MAKE AN ORIGIN OF PROBE3(IP3) IN ORDER TO ROTATE   SUP05700
DO 20 IO = 1, NB                                           SUP05710
IF(IO.EQ.IP3) GO TO 20                                     SUP05720
TX(IO) = TX(IO) - TX(IP3)                                  SUP05730
TY(IO) = TY(IO) - TY(IP3)                                  SUP05740
TZ(IO) = TZ(IO) - TZ(IP3)                                  SUP05750
CONTINUE                                                   SUP05760
TX(IP3) = 0.0D0                                            SUP05770
TY(IP3) = 0.0D0                                            SUP05780
TZ(IP3) = 0.0D0                                            SUP05790
ROTATION                                                   SUP05800
CSX = COS(X(3))                                            SUP05810
SSX = SIN(X(3))                                            SUP05820
CSY = COS(X(4))                                            SUP05830
SSY = SIN(X(4))                                            SUP05340
SCZ = COS(X(5))                                            SUP05850
SSZ = SrN(X(5))                                            SUP05860
X ROTATION                                                 SUP05870
DO 30 I = 1, 9                                             SUP05380
XROR(I) = 0.0                                              SUP05890
XROT(1) = 1.0                                              SUP05900
XROT(5) = CSX                                              SUP05910
XROT(6) = SSX                                              SUP05920
XROT(8) = SSX                                              SUP05930
XROT(9) = CSX                                              SUP05940
```

TABLE 5-continued

PROGRAMME FOR DOCKING OF TWO MOLECULES

```
DO 40 I = 1, 9                                                              SUP05950
YROT(I) = 0.0                                                               SUP05960
YROT(1) = CSU                                                               SUP05970
YROT(3) = SSY                                                               SUP05980
YROT(5) = 1.0                                                               SUP05990
YROT(7) = -SSY                                                              SUP06000
YROT(9) = CSY                                                               SUP06010
DO 50 I = 1, 9                                                              SUP06020
ZROT(I) = 0.0                                                               SUP06030
ZROT(1) = CSZ                                                               SUP06040
ZROT(2) = SSZ                                                               SUP06050
ZROT(4) = -SSZ                                                              SUP06060
ZROT(5) = CSZ                                                               SUP06070
ZROT(9) = 1.0                                                               SUP06080
DO 60 J = 1, NB                                                             SUP06090
COXX = XROT(1)*TX (J) + XROT(2)*TY(J) + XROT(3)* TZ(J)                      SUP06100
COXY = XROT(4)*TX (J) + XROT(5)*TY(J) + XROT(G)* TZ(J)                      SUP06110
COXZ = XROT(7)*TX (J) + XROT(8)*TY(J) + XROT(9)* TZ(J)                      SUP06120
COYX = YROT(1)*COXX + YROT(2)*COXY + YROT(3)*COXZ                           SUP06130
COYY = YROT(4)*COXX + YROT(5)*COXY + YROT(6)*COXZ                           SUP06140
COYZ = YROT(7)*COXX + YROT(8)*COXY + YROT(9)*COXZ                           SUP06150
CTX(J) = ZROT(1)*COYX + ZROT(2)*COYY + ZROT(3)*COYZ                         SUP06160
CTY(J) = ZROT(4)*COYX + ZROT(5)*COYY + ZROT(6)*COYZ                         SUP06170
CTZ(J) = ZROT(7)*COYX + ZROT(8)*COYY + ZROT(9)*COYZ                         SUP06180
CONTINUE                                                                    SUP06190
RETURN TO POINT P                                                           SUP06200
DO 70 I = 1, NB                                                             SUP06210
TXB(I) = CTX(I) + PX                                                        SUP06220
TYB(I) = CTY(I) + PY                                                        SUP06230
TZB(I) = CTZ(I) + PZ                                                        SUP06240
CONTINUE                                                                    SUP06250
                                                                            SUP06260
CALL ENERGY(ETOT, EV, EC, EDIS)                                             SUPOG270
RETURN                                                                      SUP06280
END                                                                         SUP06290
                                                                            SUP06300
SUBROUTINE COUL(ETOT, ER, EA)                                               SUP06310
PARAMETER (NT = 150)                                                        SUPO6320
PARAMETER (NG = 300)                                                        SUP06330
CHARACTER*2 ASYM, TITLE                                                     SUP06340
COMMON/CORD/XA(NT), YA(NT), ZA(NT), XB(NT), YB(NT), ZB(NT)                  SUP06350
COMMON/FINAL/TXB(NT), TYB(NT), TZB(NT), CA(NT), CB(NT)                      SUP06360
COMMON/INFO/NA, NB, IP1, EP2, IP3, IP4, R1, R2, CIP2, CIP4, JCON            SUP06370
ER = 0.0                                                                    SUP06380
DO 10 I = 1, NA                                                             SUP06390
X1 = XA(I)                                                                  SUP06400
Y1 = YA(I)                                                                  SUP06410
Z1 = ZA(r)                                                                  SUPO6420
DO 20 J = 1, NB                                                             SUP06430
X2 = TXB(I)                                                                 SUP06440
Y2 = TYB(I)                                                                 SUP06450
Z2 = TZB(I)                                                                 SUP06460
ER = ER + (CA(I)*CB(J))/DrST(X1, Y1, Z1, X2, Y2, Z2)                        SUP06470
CONTINUE                                                                    SUP06480
CONTINUE                                                                    SUP06490
EA = 0.0                                                                    SUP06500
X1 = XA(IP2)                                                                SUP06510
Y1 = YA(IP2)                                                                SUP06520
Z1 = ZA(IP2)                                                                SUP06530
X2 = TXB(IP4)                                                               SUP06540
Y2 = TYB(IP4)                                                               SUP06550
Z2 = TZB(IP4)                                                               SUP06560
EA = EA + (CIP2*CIP4)/DIST(X1, Y1, Z1, X2, Y2, Z2)                          SUP06570
ETOT = ER + EA                                                              SUP06580
RETURN                                                                      SUP06590
END                                                                         SUP06600
                                                                            SUP06610
SUBPROGRAM TO GENERATE ATOM TYPE AND NET ATOMIC CHARGE                      SUP06620
SUBROUTINE CHARG                                                            SUP06630
PARAMETER (NG = 300)                                                        SUP06640
PARAMETER (NT = 150)                                                        SUP06650
INTECER TYPEA, TYPEB, TYP                                                   SUP06660
COMMON/COOD/COORD(3, NG), CHARGE(NG)                                        SUP06670
COMMON/TYPE/TYPEA(NT), TYPEB(NT), TYP(NG)                                   SUP06680
COMMON/INFO/NA, NB, IP1, IP2, IP3, IP4, R1, R2, CIP2, CIP4, JCON            SUP06690
DIMENSION DCHB(35)                                                          SUP06700
DATA DCHB/0.241, 0.0, 0.515, 0.0, 0.0, -0.539, -0.490,                      SUP06710
```

TABLE 5-continued
PROGRAMME FOR DOCKING OF TWO MOLECULES

```
1 -0.267, -0.509, 0.0, -0.692, -0.54, -0.267, 0.243,              SUP06720
2 -0.135, 0.0, 0.0, 0.0, -0.622, 0.0, 0.304,                       SUP06730
3 0.0, 0.243, 0.15, 0.131, -0.516, 0.0, 0.490,                     SUP06740
4 0.0, -622, 0.515, 0.0, 0.0, 0.0, 0.0,/                           SUP06750
DO 20 I = 1, NA                                                    SUP06760
CHARGE(I) = DCHB(TYPEA(I))                                         SUP06770
CONTINUE                                                           SUP06780
SPECIAL SIDE CHAIN FOR CARBONE                                     SUP06790
CHARGES FOR HYDANTON                                               SUP06800
DO 30 I = 1, NB                                                    SUP06810
CHARGE(NA + 1) = DCHB(TYPEB(I))                                    SUP06820
CONTINUE                                                           SUP06830
CHARGE(NA + 1) = -0.36                                             SUP06840
CHARGE(NA + 2) = 0.44                                              SUP06850
CHARGE(NA + 3) = -0.41                                             SUP06860
CHARGE(NA + 4) = 0.58                                              SUP06870
CHARGE(NA + 5) = -0.31                                             SUP06880
CHARGE(NA + 6) = 0.03                                              SUP06890
CHARGE(NA + 7) = - 0.41                                            SUP06900
CHARGE(NA + 20) = 0.19                                             SUP06910
CHARGE(NA + 21) = 0.20                                             SUP06920
CHARGE(IP2) = CIP2                                                 SUP06930
CHARGE(NA + IP4) = CIP4                                            SUP06940
WRITE(6, 22) (CHARGE(I), I = 1, 12)                                SUP06950
FORMAT(3X, 6F10.4)                                                 SUP06960
RETURN                                                             SUP06970
END                                                                SUP06980
                                                                   SUP06990
SUBROUTINE SYMBOL                                                  SUP07000
PARAMETER (NT = 150)                                               SUP07010
PARAMETER (NG = 300)                                               SUP07020
CHARACTER*2 ASYM, TITLE                                            SUP07030
INTEGER TYPEA, TYPEB, TYP, HH, NN, OO, CC                          SUP07040
COMMON/COOD/COORD(3, NG), CHARGE(NG)                               SUP07050
COMMON/TYPE/TYPEA(NT), TYPEB(NT), TYP(NG)                          SUP07060
COMMON/SYMM/ASYM(NG), TITLE(40)                                    SUP07070
COMMON/INFO/NA, NB, IP1, IP2, IP3, IP4, R1, R2, CIP2, CIP4, JCON   SUP07080
DIMENSION HH(6), NN(7), OO(6), CC(10)                              SUP07090
DATA HH/5, 14, 23, 21, 24, 25/                                     SUP07100
DATA NN/8, 9, 13, 19, 26, 32, 28/                                  SUP07110
DATA OO/6, 7, 11, 12, 28, 30/                                      SUP07120
DATA CC/1, 2, 3, 1, 16, 20, 22, 27, 29, 31/                        SUP07130
NTOT = NA + NB                                                     SUP07140
DO 1 I = 1, NA                                                     SUP07150
TYP(I) = TYPEA(I)                                                  SUP07160
CONTINUE                                                           SUP07170
DO 2 I = 1, NB                                                     SUP07180
TYP(NA + 1) = TYPEB(I)                                             SUP07190
CONTINUE                                                           SUP07700
I = 0                                                              SUP07210
CONTINUE                                                           SUP07220
I - 0                                                              SUP07230
IF(I.GT.NTOT) GO TO 9                                              SUP07240
DO 20 K1 = 1, 6                                                    SUP07250
IF(TYP(I).EQ.HH(K1)) THEN                                          SUP07260
ASYM(I) = 'H'                                                      SUP07270
GO TO 10                                                           SUP07280
ENDIF                                                              SUP07290
CONTINUE                                                           SUP07300
DO 30 K1 = 1, 7                                                    SUP07310
IF(TYP(I).EQ.NN(K1)) THEN                                          SUP07320
ASYM(I) = 'N'                                                      SUP07330
GO TO 10                                                           SUP07340
ENDIF                                                              SUP07350
CONTINUE                                                           SUP07360
DO 40 K1 = 1, 6                                                    SUP07370
IF(TYP(I).EQ.OO(K1)) THEN                                          SUP07380
ASYM(I) = 'O'                                                      SUP07390
GO TO 10                                                           SUP07400
ENDIF                                                              SUP07410
CONTINUE                                                           SUP07420
DO 50 K1 = 1, 10                                                   SUP07430
IF(TYP(I).EQ.CC(K1)) THEN                                          SUP07440
ASYM(I) = 'C'                                                      SUP07450
GO TO 10                                                           SUP07460
ENDIF                                                              SUP07470
CONTINUE                                                           SUP07480
```

TABLE 5-continued
PROGRAMME FOR DOCKING OF TWO MOLECULES

```
IF(TYP(I).EQ.15) THEN                                              SUP07490
ASYM(I) = 'S'                                                      SUP07500
GO TO 10                                                           SUP07510
ELSE                                                               SUP07520
WRITE(6, 100) TYP(I), I                                            SUP07530
FORMAT(3X, 'UNDEFINED ATOM TYPE: ', I3,' ON LINE 1, I4)            SUP07540
ENDIF                                                              SUP07550
CONTINUE                                                           SUP07560
RETURN                                                             SUP07570
END                                                                SUP07580
SUBROUTINE CHEMG(NTOT)                                             SUP07590
                                                                   SUP07600
CHARACTER NAME1*2, NAME2*3, CTEMP*80, TEMP*5, ASYM*2               SUP07610
PARAXETER (NG = 300)                                               SUP07620
PARAMETER (NT = 150)                                               SUP07630
INTEGER IH, IN, IC, IO, IS, HH, NN, CC, OO, SS                     SUP07640
COMMON/COOD/COORD(3, NG), CHARGE(NG)                               SUP07650
COMMON/SYMM/ASYM(NG), TITLE(40)                                    SUP07660
                                                                   SUP07670
J = 0                                                              SUP07680
IONE = 1                                                           SUP07690
WRITE(10, 1) NTOT, IONE, IONE                                      SUP07700
FORMAT(//, I3, I5, /, I6)                                          SUP07710
                                                                   SUP07720
DO 33 I = 1, NTOT                                                  SUP07730
READ(4, '(1X, 3F10.4, 5X, A1)', END = 999) X, Y, Z, NAME1          SUP07740
X = COORD(1, I)                                                    SUP07750
Y = COORD(2, I)                                                    SUP07760
Z = COORD(3, I)                                                    SUP07770
NAME1 = ASYM(I)                                                    SUP07780
IF(NAME1.EQ. 'F') GO TO 33                                         SUP07790
J = J + 1                                                          SUP07800
IF (NAME1.EQ. 'H') THEN                                            SUP07810
IH = IH + 1                                                        SUP07820
WRITE(NAME2, '(I3)') IH                                            SUP07830
ELSEIF (NAME1.EQ. 'N') THEN                                        SUP07840
IN = IN + 1                                                        SUP07850
WRITE(NAME2, '(I3)') IN                                            SUP07860
ELSEIF (NAME1.EQ. 'C') THEN                                        SUP07870
IC = IC + 1                                                        SUP07880
WRITE(NAME2, '(I3)') IC                                            SUP07890
ELSEIF (NAME1.EQ. 'O') THEN                                        SUP07900
IO = IO + 1                                                        SUP07910
WRITE(NAME2, '(I3)') IO                                            SUP07920
ELSEIF (NAME1.EQ. 'S') THEN                                        SUP07930
IS = IS + 1                                                        SUP07940
WRITE(NAME2, '(I3)') IS                                            SUP07950
ELSE                                                               SUP07960
WRITE(6, '("You have a problem on line", I4, "in your CORD file")  SUP07970
&,')I                                                              SUP07980
ENDIF                                                              SUP07990
IF (NAME2(1:1).EQ ' ') THEN                                        SUP08000
NAME2(1:1) = NAMEI(2:2)                                            SUP08010
NAME2(2:2) = NAME2(3:3)                                            SUP08020
NAME2(3:3) = ' '                                                   SUP08030
IF (NAME2(1:1).EQ. ' ') THEN                                       SUP08040
NAME2(1:1) = NAME2(2:2)                                            SUP08050
NAME2(2:2) = ' '                                                   SUP08060
ENDIF                                                              SUP08070
ENDIF                                                              SUP08080
WRITE(10, '(I4, A2, A3, 1X, 3F10.4)') J, NAME1, NAME2, X, Y, Z     SUP08090
CONTINUE                                                           SUP08100
ENDIF                                                              SUP08110
RETURN                                                             SUP08120
END                                                                SUP08130
SUBROUTINE WRIT(X, Y, Z)                                           SUP08140
DIMENSION X(150), Y(150), Z(150)                                   SUP08150
DO 5 I = 1, 6                                                      SUP08160
WRITE(6, 10) X(I), Y(I), Z(I)                                      SUP08170
FORMAT(4X, 3F12.5)                                                 SUP08180
RETURN                                                             SUP08190
END                                                                SUP08200
                                                                   SUP08210
SUBROUTINE COMBIN (NA, NB)                                         SUP08220
DIMENSION ICON(16), IAT1(150), IAT2(150)                           SUP08230
CHARACTER*2 TT(30)                                                 SUP08240
READ(4, 10) NA                                                     SUP08250
```

TABLE 5-continued

PROGRAMME FOR DOCKING OF TWO MOLECULES

```
FORMAT(62X, I3)                                               SUP08260
READ(5, 10) NB                                                SUP08270
NTOT = NA + NB                                                SUP08280
IONE = 1                                                      SUP08290
IFOUR = 4                                                     SUP08300
TIME = 100.0                                                  SUP08310
WRITE(16, 20) NTOT, IFOUR, IONE, TIME                         SUP08320
FORMAT(60X, I5, I2, 3X, I5, F5.0)                             SUP08330
READ(4, 30) NCONA, NATA, NSPA                                 SUP08340
FORMAT(I5, 20X, I5, 15X, I5)                                  SUP08350
READ(5, 30) NCONB, NATB, NSPB                                 SUP08360
NCOT = NCONA*NCONB                                            SUP08370
NATT = NATA + NATB                                            SUP08380
NSPT = NSPA + NSPB                                            SUP08390
WRITE(16, 30) NCOT, NATT, NSPT                                SUP08400
IF(NSPA.NE.0) THEN                                            SUP08410
DO 50 I = 1, NSPA                                             SUP08420
READ(4, 40) TT                                                SUP08430
FORMAT(30A2)                                                  SUP08440
WRITE(16, 40) TT                                              SUP08450
CONTINUE                                                      SUP08460
ENDIF                                                         SUP08470
IF(NSPB.NE.0) THEN                                            SUP08480
DO 60 I = 1, NSPB                                             SUP08490
READ(5, 40) TT                                                SUP08500
WRITE(16, 40) TT                                              SUP08510
CONTINUE                                                      SUP08520
ENDIF                                                         SUP08530
DO 70 IA = 1, NCONA                                           SUP08540
READ(4, 75) (ICON(I), I = 1, 16)                              SUP08550
FORMAT(16I5)                                                  SUP08560
DO 80 IZ = 1, 16                                              SUP08570
ISZ = 16                                                      SUP08580
IF(ICON(IZ).EQ.0) THEN                                        SUP08590
ISZ = IZ - 1                                                  SUP08600
GO TO 85                                                      SUP08610
ENDIF                                                         SUP08620
CONTINUE                                                      SUP08630
WRITE(16, 75)(ICON(I), I = 1, ISZ)                            SUP08640
CONTINUE                                                      SUP08650
DO 90 IB = 1, NCONB                                           SUP08660
READ(5, 75) (ICON(I), I = 1, 16)                              SUP08670
DO 100 IZ = 1, 16                                             SUP08680
ISZ = 16                                                      SUP08690
IF(ICON(IZ).EQ.0) THEN                                        SUP08700
ISZ = IZ - 1                                                  SUP08710
GO TO 95                                                      SUP08720
ENDIF                                                         SUP08730
CONTINUE                                                      SUP08740
DO 110 I = 1, ISZ                                             SUP08750
ICON(I) = ICON(I) + NA                                        SUP08760
WRITE(16, 75)(ICON(I), I = 1, ISZ)                            SUP08770
CONTINUE                                                      SUP08780
READ(4, 75) (IAT1(I), IAT2(I), I = 1, NATA)                   SUP03790
NATA1 = NATA + 1                                              SUP08800
READ(5, 75) (IAT1(I), IAT2(I), I = NATA1, NATT)               SUP08810
DO 120 IL = NATA1, NATT                                       SUP08820
IAT1(IL) = IAT1(IL) + NA                                      SUP08830
IAT2(IL) = IAT2(IL) + NA                                      SUP08840
CONTINUE                                                      SUP08850
WRITE(16, 75) (IAT1(I), IAT2(I), I = 1, NATT)                 SUP08860
RETURN                                                        SUP08870
END                                                           SUP08880
SUBROUTINE FOR MM INPUT                                       SUP08690
SUBROUTINE MMDATA                                             SUP08900
PARAMETER (NT = 150)                                          SUP08910
PARAMETER (NG = 300)                                          SUP08920
CHARACTER*2 ASYM, TITLE                                       SUP08930
INTEGER TYPEA, TYPEB TYP                                      SUP08940
COMMON/GOOD/COORD(3, NG), CHARGE(NG)                          SUP08950
COMMON/TYPE/TYPEA(NT), TYPEB(NT), TYP(NG)                     SUP08960
COMMON/SYMM/ASYM(NG), TITLE(40)                               SUP08970
COMMON/PARAM/VEP(NG), VRA(NG)                                 SUP08980
COMMON/CORD/XA(NT), YA(NT), ZA(NT), XB(NT), YB(NT), ZB(NT)    SUP08990
COMMON/FINAL/TXB(NT), TYB(NT), TZB(NT), CA(NT), CB(NT)        SUP09000
COMMON/INFO/NA, NB, IP1, IP2, IP3, IP4, R1, R2, CIP2, CIP4, JCON  SUP09010
NTOT = NA + NB                                                SUP09020
```

TABLE 5-continued

PROGRAMME FOR DOCKING OF TWO MOLECULES

| | |
|---|---|
| WRITE(16, 20) (COORD (1, I), COORD(2, I), (COORD 3, I) TYP (I), I = 1, NTOT) | SUP09030 |
| FORMAT(2(3F10.5, I5, 5X)) | SUP09040 |
| RETURN | SUP09050 |
| END | SUP09060 |

FIGS. 2–5 show stereoscopic views of the results of docking of the receptor model with, respectively, penicillin V, $\Delta^3$-cephalosporin V, $\Delta^2$-cephalosporin V and 4-epi-$\Delta^2$-cephalosporin V. It can be seen that, in each case, the serine O—H sits on the convex face of the β-lactam compound, in such a manner as to create a four-centred interaction between O—H and (O)C—N. This four-centred interaction is shown in closer detail for penicillin V in FIG. 6.

From the Cartesian coordinates of C—O—H and (O)N—C of the optimized complexes it is possible to compute the root mean square deviations (rms) in Å of the different four centred interactions, relative to a standard substrate, in this case penicillin V. When this is done for the series of penicillins 1a–1i, it is found that all active penicillins have rms less than 0.2 Å, and all inactive penicillins have rms greater than 0.4 Å. For the series shown in FIGS. 2–5, the rms deviations are 0.000, 0.149, 0.338 and 0.148 Å. This implies that the "fits" of the biologically active $\Delta^3$-cephalosporin and the biologically inactive 4-epi-$\Delta^2$-cephalosporin to the penicillin receptor are identical. The biologically inactive $\Delta^2$-cephalosporin has a poorer fit.

The biological activity of a drug depends not only on its ability to fit to a receptor, i.e., Step 1 of equation 1, but also on its ability to react chemically with the receptor, i.e., Step 2 of equation 1. The chemical reaction suggested by FIGS. 2–6 is a four centred process in which C7-0(Ser) (see A) and N—H(Ser) bond formation are concerted. This is an unprecedented chemical mechanism.

The hydrolysis and alcoholysis of β-lactam compounds has received much experimental and theoretical attention. In water above pH 8, the rate-determining step is addition to the carbonyl group to form a tetrahedral intermediate; below pH 6, there is rate-determining proton transfer to the β-lactam nitrogen, from the convex face of the molecule. Hydrolysis is extremely slow in the biologically relevant pH range 6–8, and the possible existence of a molecular (four-centred) mechanism in this region has not been established. Likewise, all previous theoretical studies of β-lactam hydrolysis have emphasized anionic addition to the β-lactam carbonyl group.

Molecular orbital (MO) calculations of the ab initio type represent an accepted and well established procedure for the probing of the mechanisms of chemical reactions. Such calculations can be performed using low level (STO-3G) and high level (3–21G) basis sets using the computer programmes GAUSSIAN 82 and GAUSSIAN 86, available from GAUSSIAN Inc., Pittsburgh, Pa, U.S.A. Molecular orbital calculations of the semi-empirical type can be performed on relatively large molecular systems, and are valid once they have been calibrated with respect to an ab initio calculation on the same system. The semi empirical procedures AM1, MNDO and MINDO/3 are available in the computer programme AMPAC, available from QCPE.

Table 6 summarizes the ab initio data ($\Delta\Delta E\ddagger$, kcal/mol) for the reactions of N-methylazetidinone with water and with methanol via exo-oriented N- and O-protonated structures. For the hydrolysis reactions, the O-protonated structure is favoured by 1.75 kcal/mol at the lower STO-3G level (STO- 3G//STO-3G). One point calculations at the more appropriate 3–21G level (3–21G//3–21G) increases the preference for the N-protonated transition structure to 5.66 kcal/mol. Analogous results are seen for methanolysis of N-methylazetidinone. These results prove that the four-centred interaction seen in FIGS. 2–6 reflects a genuine chemical process and, indeed, the energetically preferred chemical process. The N- and O-protonated methanolysis transition structures are shown in FIGS. 7 and 8, respectively.

Table 6 also summarizes the semi-empirical results for the hydrolysis and methanolysis of N-methylazetidinone, and it is evident that only MINDO/3 correctly reproduces the preference for the N-protonated transition structure. Accordingly, MINDO/3 was used to examine the activation energies for the reactions of a large number of bicyclic azetidinones with methanol. These are summarized in Table 7.

TABLE 6

Relative E* for the Hydrolysis and Methanolysis of N-Methylazetidinone via N- and O-Protonated Transition Structures.[a]

| TS | STO-3G | 3-21G//STO-3G | 3-21G//3-21G | AM1 | MNDO | MINDO/3 |
|---|---|---|---|---|---|---|
| | | | Hydrolysis | | | |
| N | 1.75 | 0.00 | 0.00 | 8.46 | 7.31 | 0.00 |
| O | 0.00 | 4.41 | 5.66 | 0.00 | 0.00 | 1.81 |
| | | | Methanolysis | | | |
| N | 2.26 | 0.00 | | 9.21 | 7.86 | 0.00 |
| O | 0.00 | 4.39 | | 0.00 | 0.00 | 1.20 |

[a]Relative energies are in kcal/mol.

Within each row of Table 7, the reactions of the different structural types are compared to that of the parent penam ring system of penicillin, and the data are discussed row-by-row: (1) the relative reactivities are carbapenam>penem>oxapenam>penam. Oxapenicillins and penems having the C3 and C6 substituents of penicillins are known to have antibacterial activity; although the carbapenam ring system is known, carbapenicillins have not yet been prepared. (2) in the comparison of the penam and cephem ring systems, the relative reactivities are penam>>Δ-cephem>Δ$^2$-cephem, acetoxymethyl-Δ$^3$-cephem. With a common acylamino side chain, penicillins are an order of magnitude more active than acetoxymethyl-Δ$^3$-cephalosporins and the latter are, in general, an order of magnitude more active than 3-methyl Δ$^3$-cephems; Δ$^2$-cephems are inactive. (3) introduction of the C3α-carboxyl group enhances the reactivity. It is believed that the carboxyl group assists the methanolysis through hydrogen bonding, because epimerization (C3β) decreases the reactivity significantly. (4) introduction of C2-methyl substituents decreases the reactivity, unless a C3α-carboxyl group is present. (5) the 6β-acylamino substituent has almost no effect on the reactivity. Consequently, the chemical reactivity of a penicillin differs only slightly from that of the parent penam.

FIGS. 9–11 show, respectively, stereoscopic views of the N- and O-protonated transition structures for exo-methanolysis of a penicillin, and O-protonated endo-methanolysis of penam. Such endo-oriented transition structures are ca 1 kcal/mol higher in energy than the O-protonated exo-structures and 5–6 kcal/mol higher in energy than the N-protonated exo-structures.

Table 8 summarizes the "fits" of penicillin V and 2a–2c mentioned above, as well as the "reactivities" of the different ring systems, as given by ΔΔE‡ for the reaction of methanol with the carboxylated substrates shown.

The product rms×ΔΔE‡ represents a combination of fit and reactivity, and is seen to order correctly the different classes of antibiotics in the order of their biological activities. Based on this quantity, 2b is inactive because of its poorer fit to the receptor, and 2c is inactive because of its decreased reactivity.

The difference between 2b and 2c can be compared to the differences seen in Row 3 of Table 7. That difference is attributed to facilitation of the chemical process by hydrogen bonding of the attacking alcohol to the carboxyl group when this group is on the convex face of the molecule. Thus 2c recovers the fit lost in 2b but concomitantly becomes less reactive. These considerations suggest that the attachment of a hydrogen bonding donor substituent on the convex face of 2c will restore the chemical reactivity while retaining the acceptable fit to the receptor. Possible sites for the attachment of the required substituent are sulfur, C4 and C7 (see Table 8$^d$ for numbering). Attachment of F, CH$_3$O and CH$_2$OH to C4 and C7 in the required manner does not enhance the reactivity of 2c, but an alpha-oriented sulfoxide (3) exhibits reactivity superior to that of penicillin. Although a malonic acid derivative which combines the favourable properties of 2b and 2c (4) exhibits somewhat reduced reactivity compared to penicillin (ΔΔE‡=3.51 kcal/mol), the product rms×ΔΔE‡ is intermediate between the active and

TABLE 7

Calculated ΔΔE‡ (kcal/mol, MINDO/3) Relative to N-Methylazetidione for the Methanolysis of β-Lactam Compounds via Exo Formation of a Four-Centred N-Protonated Transition Structure Row 1: −2.80, −4.15, −4.11, −3.56
Row 2: −2.80, −0.25, 0.44 (OAc), 0.46
Row 3: −2.80, −3.86 (CO$_2^-$), −2.35 (CO$_2^-$)
Row 4: −2.80, −2.45, −2.93 (CO$_2^-$)
Row 5: −2.80, −2.73 (HCONH), −2.62 (HCONH, CO$_2^-$)

inactive entries of Table 8. Accordingly, 3 and 4 are novel β-lactam containing structural types of potential biological interest.

TABLE 8

Root Mean Square (rms) Difference (Å), Relative to Penicillin V, of the Cartesian Coordinates of the C—O—H Atoms of Serine and the N—C=O Atoms of the Azetidinone Ring in the Complexes of β-Lactam Compounds with a Model of the Penicillin Receptor; Activation Energies (kcal/mol) for the Reaction of Azetidinones with Methanol, Relative to the Penam Nucleus; and the Product rms x ΔΔE‡.

| substrate | rms | ΔΔE‡ | rms × ΔΔE‡ |
|---|---|---|---|
| 2a | 0.149 | 2.81[a] | 0.42 |
| penicillin V | 0.000 | 0.00[b] | 0.00 |
| 2b | 0.338 | 1.94[c] | 0.66 |
| 2c | 0.148 | 4.65[d] | 0.69 |

[a]Refers to MINDO/3 calculations on 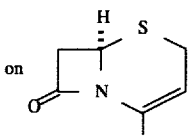

[b]Refers to MINDO/3 calculations on 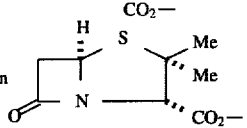

[c]Refers to MINDO/3 calculations on 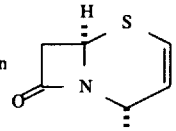

[d]Refers to MINDO/3 calculations on 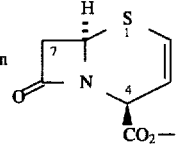

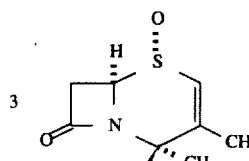

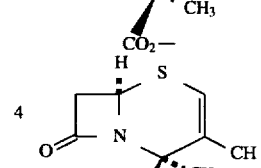

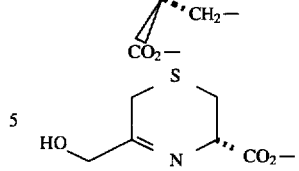

It is also possible to design entirely new structural types compatible with the combination of fit and reactivity developed here. Based on the dihedral angles of penicillin V, a carboxyl group oriented so that it makes a dihedral angle of 150°–160° with a "reactive site", and a hydrogen bonding donor such as N—H or O—H oriented so that it makes a dihedral angle of −150 to −160° with the "reactive site" is required. The reactive site should be one that reacts with methanol via a four-centred transition structure, and with ΔE ‡ no greater than 3–4 kcal/mol higher than that for the reaction with an azetidinone.

Systematic calculation of activation energies has identified the imino moiety

as a functional group possessing the required reactivity, and incorporation of this moiety into a cyclic structure possessing dihedral angles of the required magnitude has identified 5 as a candidate structure having antibacterial activity by a penicillin-cephalosporin mechanism. The result is shown in FIG. 12.

EXAMPLE 1

Application of PEPCON to the Calculation of the Polypeptide Crambin

This polypeptide contains 46 amino acid residues, 327 heavy atoms, and 636 atoms including hydrogens. The published crystal structure includes diffraction data refined to 1.5 Å. The cartesian coordinates of the heavy (non-hydrogen) atoms of this crystal structure were used as input to MMP2(85), hydrogens were added using an option available in MMP2(85), and Newton-Raphson minimization was performed using PEPCON. The calculated structure shows an rms deviation from the experimental structure of 0.291 Å for the heavy atoms of the backbone, and 0.310 Å for all heavy atoms.

EXAMPLE 2

Application of PENCON to the Calculation of Penicillin V

Repetition of the experiment of Example 1, with the cartesian coordinates of the crystal structure of penicillin V and the PENCON parameters leads to an rms deviation of 0.1 Å for all atoms.

EXAMPLE 3

Application of CEPARAM to the Calculation of Cephalosporin

The cartesian coordinates of the crystal structure of a $\Delta^2$-cephalosporin having the phenoxyacetyl side chain were entered, and the energy was minimized using MMP2(85) in conjunction with the CEPARAM parameters. The resulting rms deviation was 0.35 Å.

EXAMPLE 4

Application of the Random Number Strategy and ECEPP to the Conformational Analysis of a Peptide The peptide Gly-Trp-Met-Asp-Phe-NH$_2$ was entered into ECEPP, and an initial search was performed on 200,000 initial conformations of this molecule. The fifty lowest energy structures identified in this manner were minimized in ECEPP using a quadratic minimization procedure, and then refined using the PEPCON parameters of MMP2(85). One structure was strongly preferred, and the dihedral angles of this structure are identical to those of the gastrin tetrapeptide, which contains the Trp-Met-Asp-Phe-NH$_2$ moiety of the above compound.

EXAMPLE 5

Calculation of the Structure of a Penicillin Receptor.

The peptide Ac-Val-Gly-Ser-Val-Thr-Lys-NHCH$_3$ was treated as described in Example 4, and the fifty final structures were examined. Only one structure possessed lysine and serine side chains on the same side of the molecule. This structure is shown in FIG. 1, and its dihedral angles are summarized in Table 4.

EXAMPLE 6

Docking of Penicillin V to a Model of the Penicillin Receptor

The receptor model of Example 5 was docked to penicillin V using the computer program of Table 5. Several conformations of the penicillin were examined, and the final lowest energy complex is shown in FIG. 2.

The invention will be further illustrated by way of the following specific examples of compounds that have been prepared:

EXAMPLE 7

Synthesis of 3-Carboxy-5-Hydroxymethyl-6, 6 -Dimethyl-Δ4-1, 4-Thiazine

In formula I, X=S; Y=OH; R$_1$=R$_2$=CH$_3$, R$_3$=R$_4$=H. Both D- and L- configurations at C$_3$ are prepared.

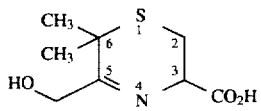

STEP 1

Methyl isopropyl ketone (15 mL, 140 moles) was added to a solution of potassium chloride (1.1 g, 14.8 moles) in water (9.6 mL). The mixture was stirred, warmed to 60° C., and illuminated with a 350 watt tungsten lamp mounted beside the flask. Bromine (11.9 g, 74.4 moles) was then added dropwise. When the colour of the first few drops had disappeared, the heating bath was replaced by a cold water bath, and the 350 watt bulb was replaced by a 60 watt bulb. Addition of bromine was continued at a rate sufficient to maintain the internal temperature at 40°–45° C. When the addition was complete (25 min) the reaction mixture was allowed to stand for 2 h and the orgainic phase was then separated, washed with wwater-magnesium oxide and dried over anhydrous calcium chloride. Fractional distallation afforded 7 g of Al, b.p. 82°–86°/145 torr. NMR (CDCl$_3$) 2.36 (3H, s), 1.77 (6H, s).

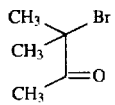

STEP 2

The bromeketine Al (4.65 g, 28 moles) was dissolved in glacial acetic acid (40 ml), and freshly recrystallized lead tetraacetate (12.5 g, 28.2 moles) was added. The mixture was heated at 100° C., with stirring, for 2 h and cooled to room temperature. Ethylene glycol (2 mL) was then added to destroy unreacted lead tetraacetate. The reaction mixture was diluted with ether (100 mL), washed successively with 10% sodium carbonate, water and saturated sodium chloride, dried and evaporated. The residue was distilled, and the fraction boiling at 57°–60° C./120 torr was further purified by chromatography (silica gel, 5%>10%–>15% ether-hexane) to give the bromoketoacetate B1. NMR (CDCl$_3$: 5.16 (2H, s), 2.13 (3H, s), 1.87 (6H, s).

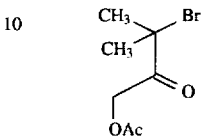

STEP 3

Triethylamine (140 mL) was added to methylene chloride (3 mL). The solution was cooled to –20° C., and gaseous hydrogen sulfide was introduced during 10 min. Then the bromoketoacetate B1 (200 mg), in methylene chloride (1.0 mL), was added dropwise with stirring during 10 min. The yellow solution was diluted with methlene chloride (30 mL)30, washed successively with 2N hydrochloric acid, water and saturated sodium chloride, dried over anhydrous sodium sulfate and evaporated to yield the mercaptoketoacetate C1. NMR (CDCl$_3$) 5.16 (2H, s), 2.18 (3H, s), 1.57 (6H, s), 1.55(1H, s).

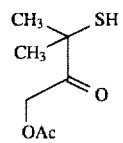

STEP 4

To triphenylphosphine (258 mg, 0.98 mole) in dry tetrahydrofuran (1.0 mL0, at –78° C. under a nitrogen atomosphere, was added dropwise with stirring a solution of dimethylacetylenedicarboxylate (144 mg, 0.99 mole) in tetrahydrofuran (1.0 mL). The white slurry as maintained at –78° C. for 10 min, and a solution of Boc-L (or D-)-serine (184 mg, 0.90 mole) in tetrahydrofuran (1.0 mL) was added dropwise. The temperature was maintained at –78° C. for 20 min and the reaction mixture was then allowed to warm to room temperature (2 h). The solvent was removed and the residue was chromatographed on silica gel. Elution with 15%–>22%–30%–>35% ethyl acetate-hexane afforded the beta-lactone D1. NMR (CDCl$_3$) 5.29 (1H, br), 4.92 (1H, br), 4.34 (2H, br), 1.07 (9H, s) .

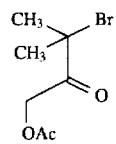

STEP 5

To a solution of C1 (79.6 mg, 0.45 mole) in dry degassed dimethylformamide (1.5 mL) was added dropwise a solution of lithium diisopropylamide (0.8 mole) in tetrahydrofuran (1.5 mL). The addition was carried out under nitrogen at –60° C. The reaction mixture was allowed to warm to –25° C. during 50 min, cooled again to –55° C., and a solution of D1 (56.4 mg, 0.30 mole) in dry degassed dimethylformamide (0.5 mL) was added dropwise. When the addition was complete, the mixture was warmed to −20° C., stirred for 25 min and then diluted with ethyl acetate (30 mL) and washed with 0.5N hydrochloric acid (2 mL). The aqueous layer was extracted with ethyl acetate (2×10 mL) and the combined organic extracts were washed with water (2×5 mL) and saturated sodium chloride (1×5 mL), dried and evaporated. The oily residue was purified by preparative layer chromatography on a 10×20 cm plate coated with silic gel, using methylene chloride-ethyl acetate acetic acid (1.7:0.3:0.05) as eluant to give E1 (77 mg, 70.3%). NMR (CDCl$_3$) 5.43 (1H, br), 5.20 (1H, d, 18 Hz), 5.04 (1H, d, 18 Hz), 4.46 (1H, br), 2.97 (1H, br), 2.78, 2.74 (1H, dd, 4.5, 9.0Hz), 2.17 (3H, s), 1.48(3H, s), 1.47 (3H, s), 1.44 (9H, s).

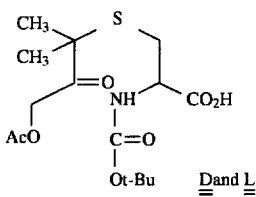

E1

STEP 6

The acid E1 (77 mg) was dissolved in methylene chloride (10 mL) and treated at 0° C. with an ethereal solution of diazomethane. The solvent was removed and the residue was purified on a 5×10 cm silica gel plate using hexane-ethyl acetate (1.4:0.6) as eluant to give the ester F1 (48.2 mg). NMR (CDCl$_3$) 5.32 (1H, br d), 5.15 (1H, d, 11Hz), 5.07 (1H, d, 11Hz), 4.48 (1H, br, q), 3.76 (3H, s), 2.91 (1H, q, 4, 12Hz), 2.74 (1H, q, 5.5, 12 Hz), 1.47 (6H, d), 1.44 (9H, s).

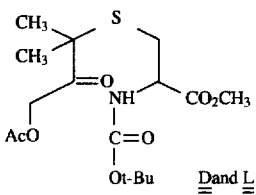

F1

STEP 7

The ester F1 (46 mg), in tetrahydrofuran (1 mL) was treated at room temperature with 0.25M lithium hydroxide (0.4 mL). After 25 min an additional 0.4 mL of lithium hydroxide was added. The mixture was stirred for 35 min and then diluted with ethyl acetate (10 mL) and washed with 0.5N hydrochloric acid (2×5 mL). The aqueous layer was extracted with ethyl acetate (2×5 mL) and the combined organic extracts were washed with water (1×5 mL), followed by saturated sodium chloride (1×5 mL), dried and evaporated. The residue was dissolved in the minimum of methylene chloride, treated with ethereal diazomethane, concentrated, and the residue was purified on a 10×20 cm silica gel plate. Elution with hexane-ethyl acetate (1.4:0.6) gave G1 (14.4 mg). NMR (CDCl$_3$) 5.22 (1H, br), 4.58 (2H, d), 4.48 (1H, br), 3.75 (3H, s), 3.06 (1H, br), 2.92 (1H, br), 2.74 (1H, dd, 5, 11Hz), 1.46 (9H, s), 1.44 (6H, s).

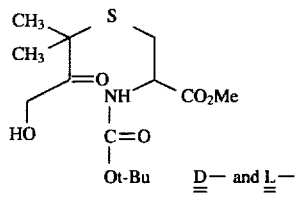

G1

STEP 8

To a solution of G1 (5 mg, 0.015 mole) in freshly dried pyridine (0.2 mL) were added successively silver nitrate (3.4 mg, 0.02 mole) and t-butyldiphenylchlorosilane (6.3 mg, 0.023 mole). The solution was stirred for 15 min at room temperature under nitrogen. The solvent was then removed and the product was purified by preparative layer chromatography to give H1 (5.5 mg). NMR (CDCl$_3$) 7.69 (4H, m), 7.41 (6H, m), 5.07 (1H, br), 4.70 (2H, s), 4.41 (1H, br), 3.72 (3H, s), 2.70 (1H, dd), 2.55 (1H, dd), 1.43 (9H, s), 1.28(3H, s), 1.26(3H, s), 1.10 (9H, s).

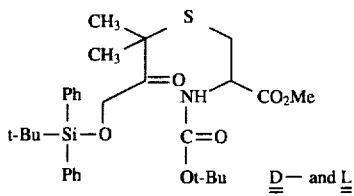

H1

STEP 9

The silyated ester H1 (5 mg) was treated at room temperature with formic acid (0.2 mL). After 33 min the reaction mixture was frozen and the solvent was removed by lyophilization to yield the enamine 11. NMR (CDCl$_3$): 7.69 (4H, m), 7.40 (6H, m), 5.90 (1H, s), 4.65 (1H, br), 3.79 (3H, s), 3.76 (1H, br), 3.17 (1H, dd, 10, 15Hz), 3.00(1H, dd,3,15 Hz), 1.49(3H, s), 1.31(3H, s), 1.08(9H, s).

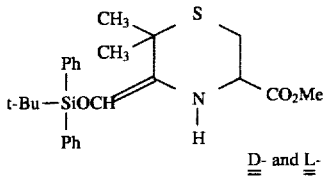

11

STEP 10

The thiazine 11 was treated with lithium hydroxide, as described in Step 7, to remove the ester protecting group. The silylated protecting group was also removed in part to afford a reaction mixture which contained 3-carboxy-5-hydroxymethyl-6,6-dimethyl 4-1,4-thiazine.

EXAMPLE 8

Synthesis of 3-Carboxy-5-(2-Hydroxypropyl)-6,6-Dimethyl-4-1,4-Thiazine

In formula II, X=S; Y=OH; $R_1$=$R_2$=CH$_3$; $R_3$=$R_4$=$R_6$=$R_7$=H; $R_5$=CH$_3$. Both D- and L- configuration at C3 are prepared, but the R- and S- epimers at C8 have not been separated; the D- isomer is active.

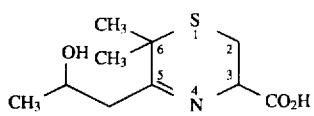

STEP 1

A solution of ethyl 2-methylcyclopropanecarboxylate (5.0 g, 38.9 moles) in dry ether (5 mL0 was added dropwise, with stirring under nitrogen, to the Grignard reagent prepared from magnesium turnings (1.935 g, 0.080 g-atom) and methyl iodide (12.43 g, 87.6 moles) in dry ether (42 mL). The addition required 30 min; stirring was continued for 2.75 h at room temperature and then for 2 h under reflux. The reaction mixture was cooled in an ice-bath and saturated ammonium chloride (10 mL) wass added, with stirring. The layers were separated and the aqueous layer was extracted with ether (2×20 mL). The combined organic phase was dried, evaporated and the residue distilled at 132°–136° C. to give the tertiary alcohol A2 (4.24 g, 95%)

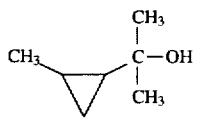

STEP 2

To the alcohol A2 (4.24 g, 37 moles) cooled in an ice-bath, was added ice-cold 48% hydrobromic acid (15 mL). The mixture was shaken vigorously in the ice-bath for 30 min. The two layers were then separated, the aqueous layer extracted with hexane (2×20 mL), and the combined organic phase was washed successively with saturated bicarbonate (2×10 mL), wate2 (2×10 mL) and saturated sodium chloride (2×10 mL), dried over anhydrous sodium sulfate, and evaporated. Distillation afforded 3.72 g (60%0 of the bromine B2, b.p. 46°–54° C./10 torr.

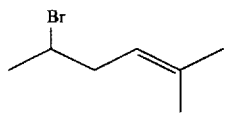

STEP 3

To a solution of the bromide B2 (3.72 g, 21 moles) in glacial acetic acid (20 mL) was added potassium acetate (3.1 g, 31.6 moles). The mixture was heated under reflux for 12 h, cooled, and poured into water (30 mL). Extraction with ether (3×30 mL), followed by succesive washing of the organic phae with aturated sodium carbonate, water and saturated sodium chloride, drying, and evaporation at room temperature yclded the acetate C2, 2.82 g (85%). NMR CDCl$_3$) 5.10 (1H, brt), 4.88 (1H, q, 6Hz), 2.30 (1H, m), 2.19 (1H, m), 2.02 (3H, s), 1.71 (3H, br s), 1.62 (3H, br s), 8.00 (3H, d, 6Hz).

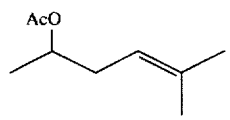

STEP 4

The acetate C$_2$ (320 mg, 2.05 moles) was dissolved in methanol (2 mL) and treated dropwise with a 1.5M solution of potassium hydroxide in methanol (1.38 mL). The reaction mixture was allowed to stand for 6 h and was then neutralized with 1.5 Mmethanolic hydrogen chloride, and the solvent was removed. The residue was dissolved in methylene chloride, and this solution was washed successively with water and saturated sodium chloride, dried and evaporated to give the alcohol D2 (208 mg, 99%).

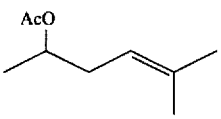

STEP 5A

The alcohol D2 (312 mg, 2.73 moles) was dissolved in dimethylformamide (2 mL) and to this solution were added successively t-butylidemethylchlorosilane (535 mg, 3.55 moles). The mixture was stirred for 2 h and then filtered. The insoluble material was triturated with ether (20 mL) and the combined organic material was washed successively with saturated sodium bicarbonate, water and saturated sodium chloride, dried and evaporated to give the silyated compound E2A (620 mg, 100%).

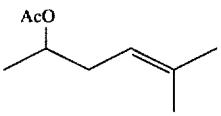

STEP 5B

The alcohol D2 (25 mg, 0.22 mole) was dissolved in dimethylformamide (0.2 mL), and the solution was treated successively with pyridine (27 1, 0.33 mole), t-butyldiphenylchlorosilane (90 L, 0.35 mole) and silver nitrate (56 mg, 0.33 mole). The mixture was stirred at room temperature for 4 h, and the product was then isolated, as described in Step 5A, to yield E2B.

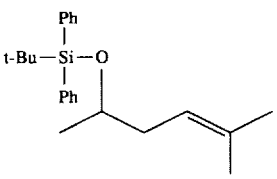

STEP 6A

The olefin E2A (624 mg, 2.73 moles) was dissolved in acetine (3 mL) and 18-crown-6 (100 mg, 0.27 mole) and acetic acid (0.16 mL) were added successively followed, dropwise, by a solution of potassium permanganate (603 mg, 3.82 moles) in water (7.5 mL). The mixture wa stirred for 1 hr and then diluted with methylene chloride (50 mL0. The organic phase was washed successively with 20% sodium bisulfite, 0.5N hydrochloric acid, saturated sodium bicarbonate, water and saturated sodium chloride, dried and evaporated. The residue wa subjected to flash chromatography on silical gel (7 g). Elution with 4→15% ethyl acetate-hexane gave 479 mg (70%) of the ketol F2A.

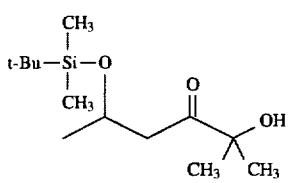

F2A

STEP 6B

The olefin E2B (77.5 mg, 0.22 mole) was oxidized with potassium permangamate, as described in Step 6A, to yield the ketol F2B. NMR (CDCl₃): 7.72 (4H, m), 7.43 (6H, m), 4.43 (1H, q, 6Hz), 3.81 (1H,s), 2.81 (1H, dd, 5, 16Hz), 2.58 (1H, dd, 7, 16Hz), 1.31 (3H, s), 1.29 (3H, s), 1.10 (3H, d, 5Hz), 1.04 (9H, s)

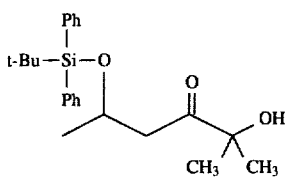

F2B

STEP 7A

To a solution of the ketol F2A (478 mg, 1.83 moles) in methylene chloride (6 mL) were aded successively triethylamine (0.76 mL, 4.0 moles) and methanesulfonyl chloride (0.24 mL, 3.1 moles). The reaction mixture was stirred for 5 h at room temperature and then diluted with methylene chloride (80 mL). The solution was washed successively with water, 0.5N hydrochloric acid, saturated sodium bicarbonate, water and saturated sodium chloride, dried and evaporated. Flash chromatography on silica gel (3 g) and elution with 7%–>8%–>9%–>10% ethyl acetate-hexane gave G2A (432 mg, 70%).

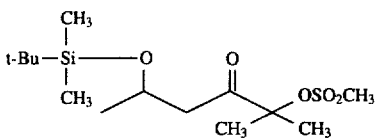

G2A

STEP 7B

The ketol F2B (277 mg, 0.72 mole) was converted into the mesylate G2B (233 mg), as described in Step 7A. NMR (CDCl₃) 7.71 (4H, m), 7.41 (6H, m), 4.44 (1H, dq), 3.08 (3H, s), 2.95 (1H, dd, 6, 18Hz), 2.27 (1H, dd, 7, 18Hz), 1.63 (3H, s), 1.61 (3H, s), 1.15 (3H, d, 6Hz), 1.06 (9H, s).

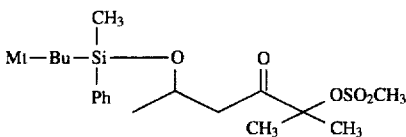

G2B

STEP 8A

Methylene chloride (5 mL) was saturated with hydrogen sulfide at −20° C., and triethylamine (0.14 mL, 1 mole) and a solution of the mesylate G2A (233 mg, 0.5 mole) were added successively. The solution was stirred for 10 min at −20° C. and for 45 min at −20° C.–>0° C., and was then diluted with methylene chloride (30 mL), washed successively with 0.5N hydrochloric acid, water and saturated ssodium chloride, dried and evaporated to give, after drying at 0.1 torr, the mercaptan H2A (170 mg, 85%). NMR(CDCl₃) 4.37 (1H, m), 2.98 (1H, dd, 5, 11Hz), 2.63 (1H, dd, 4, 11Hz), 1.98 (1H, s), 1.49 (3H, s), 1.48 (3H, s), 1.17 (3H, d, 5Hz), 0.84 (9H, s), 0.05 (3H, s), 0.01 (3H, s).

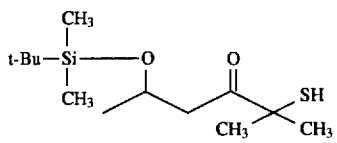

H2A

STEP 8B

The mesylate G2B was converted into the mercaptan H2B as described in Step 8A. NMR (CDCl₃) 7.71 (4H, m), 7.40 (6H, m), 3.00 (1H, dd, 6, 16Hz), 2.75 (1H, dd, 7, 16Hz), 1.93 (1H, s), 1.46 (3H, s), 1.45 (3H, s), 1.13 (3H, d, 6Hz), 1.05 (9H, s)

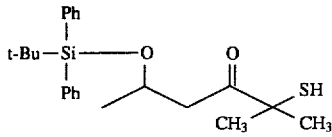

H2B

STEP 9

Under nitrogen, the nercaptan H2A (100 mg, 0.36 mole) was dissolved in degassed dimethylormamide (1.0 mL). The solution was cooled to −55° C. and treated with 0.45 mL of a solution of lithium diisopropylamide prepared from n-butyllithium (0.8 mL of a 1.6M hexane solution) and diisopropylamine (0.36 mL, 0.259 g, 2.56 moles) in degassed tetrahydrofuran (0.8 mL). The reaction mixture was stirred at −45° C. for 30 min, and a solution of the beta-lactone D1 (D- or L) (56.8 mg, 0.30 mole) in degassed dimethylformamide (0.8 mL) was added. The mixture was stirred at −30° C. for 20 min and then diluted with methylene chloride (10 mL0 and washed with 0.5N hydrochloric acid. The aqueous layer was extracted with methlene chloride (2×5mL) and the combined organic extracts were washed with water, then saturated sodium chloride, dried and evaporated. The residue was dried under high vacuum and purified by flash chromatography (silica gel, 4 g; 0%–>8% ethyl acetate-methylene chloride (1% acetic acid)) to give the coupled product 12D or 12L 12D (88.6%, [ ]D−2.27 (c 0.1, chloroform)). NMR (CDCl₃) (one isomer) 5.28 (1H, br t), 4.48 (1H, br) 4.32 (1H, m), 2.83, 2.71 (2H, m), 2.71, 2.62 (2H, m), 1.44 (9H, s), 1.43 (6H, s), 1.16 (3H, d, 6Hz), 0.85 (9H,), 0.05 (3H, s), 0.00 (3H, s). The nmr spectrum shows a 1:1 mixture of epimers in the 2-hydroxypropyl side chain.

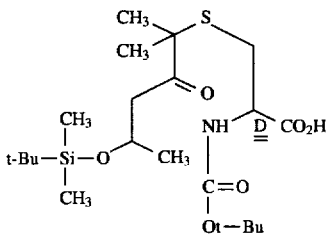

12D 12L (83%, [ ]D+2.33 (c 0.1, chloroforum)). NMR (CDCl₃) (one isomer) 5.28 (1H, br t), 4.48 (1H, br), 4.32 (1H, m), 2.86, 2.79 (2H, m), 2.70, 2.61 (2H, m), 1.43 (9H, s), 1.42 (6H, s), 1.16 (3H, d, 6Hz), 0.83 (9H,s), 0.04 (3H, s), 0.00 (3H, s). The nmr spectrum shows a 1:1 mixture of epimers in the 2-hydroxypropyl side chain.

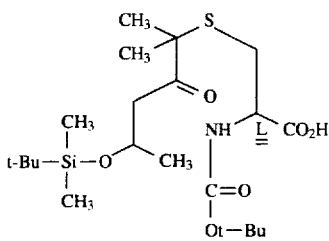

STEP 10A

To 12D (22.7 mg, 0.049 mole) was added formic acid (0.3 mL). The solution was shaken for 20 min at room temperature and the solvent was then removed by lyophilization. The residue wa dissolved in a mixture of ether (3 mL) and water (1 mL). The ether phase was extracted with water (1 mL), and the combined aqueous phase wa neutralized with 5% sodium bicarbonate and lyophilized to give 2(5 mg, 40%) having the D-configuration at C3, as a mixture of epimers in the 2-hydroxypropyl side chain. NMR (D2O) 4.23 (1H, m), 3.80 (1H, m), 3.30 (1H, q), 2.70–2.85 (3H, m), 1.40 (6H, s), 1.15(3H, d).

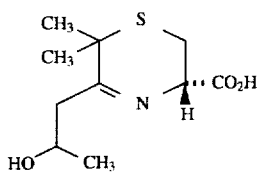

STEP 10B

The procedure of Step 10A was repeated on 12L to give 2 having the L-configuration at C3

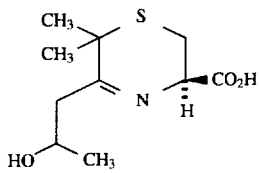

EXAMPLE 9

Bioassy of 2-D

The compound was assayed for antibacteral activity in plates inoculated either with *Sarcina lutea* or *Escherichia coli*. In the former case, penicillin G was employed as a standard. In the latter case, Cephalexin was employed as the standard. The compound was found to be 800 times less active than penicillin G, and 10 times less active than Cephalexin. The L-isomer of 2 was found to be inactive in both assays.

EXAMPLE 10

Synthesis of 2-Thia-4-Carboxy-6-(2-Hydroxypropyl)-7,7-Dimethyl-5-1,5-Thiazepine.

In formula III, X—Y=S—S; Z=OH; $R_1=R_2=CH_3$; $R_3=R_4=R_5=R_6=R_7=CH_3$. Both D- and L- configurations of $C_4$ are prepared, but the R- and S- isomers at C9 have not been separated. The L-isomer is active (FIG. 13)

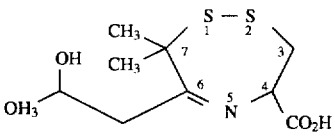

L-Cysteine hydrochloride (4.1 mg, 0.026 mole) was dissolved in 90% methanol-water (0.35 mL), and a solution of the mercaptan H2A (Example 2, Step 8A) (7.1 mg, 0.026 mole) in methanol (0.35 mL) wa added, followed by iodine (6.5 mg, 0.026 mole) and triethylamine (7 L, 0.050 mole). The reaction mixture was left for 30 min at room temperature and the solvent was then removed under reduced pressure. The residue was partitioned between pH 7 phosphate buffer (containing one drop of 10% sodium thiosulfate) and methylene chloride. The aqueous layer was extracted with ethyl acetate (1×5 mL) and lyophilized. The residue was triturated with methanol, and the methanol extract was combined with methylene chloride and ethyl acetate extracts and evaropated. The product was purified on 10×15 cm alumina plate using methylene chloride-methanol-water (1.8:0.2:0.15) as eluant to give the disulfide A4-L (8.9 mg, 80%). NMR (D$_2$O): 4.19 (1H, m), 3.92 (1H, dd, 3.7 Hz), 3.18 (1H, m), 3.04 (1H, m), 2.92 (1H, m), 2.76 (1H, m), 1.43 (6H, s), 1.12 (3H, d, 7Hz). The compound is a mixture of epimers in the 2-hydroxypropyl chain.

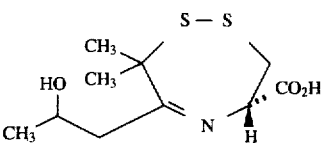

Repetition of this experiment using D-cysteine in place of L-cysteine gave A4-D.

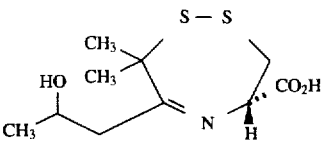

The amino acids A4-D and A4-L were dissolved in water containing sodium bicarbonate and asayed for antibacterial activity by plate assay using S. lutea. A zone of inhibition was observed with the L-isomer, but not with the D-isomer. The inhibition is ascribed to the formation of the cyclic tructure 3L, whose interaction with the model of the penicillin receptor is shown in FIG. 13.

EXAMPLE 11

Synthesis of 3-Carboxy-5-Oximino-1,4-Thiazine

In formula IV, X=S; $R_1=R_2=CH_3$; $R_3=R_4=R_9=H$; X=N; Z=OH. Both D- and L- isomers at C3 are ??.

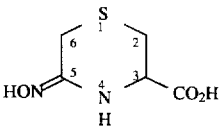

STEP 1

To a solution of D-cysteine (605.8 mg, 5 moles) in methanol (10 mL) were added uccessively ethyl bromoacetate (0.99 g, 5.95 moles) and triethylamine (1.4 mL, 1.02 g, 10 moles). The solution was stirred for 20 min at room temperature and ether (20 mL) was then added. The product was collected by filtration, washed with ether and dried. Five hundred mg of tthis material were suspended in dimethylformamide (5 mL), and p-toluenesulfonic acid (458 mg, 2.41 moles) was added. The reulting solution wa treated portionwise with diphenyldiazomethane until the color of the diazo compound persisted, and the reaction mixture was stirred overnight. It was then diluted with ether (20 mL) and extracted with water (2×10 mL). The aqueous extract was made alkaline by addition of saturated sodium carbonate, and was then extracted with ethyl acetate (3×10 mL). The combined organic extracts were washed with water and saturated sodium chloride, dried and evaporated. A 370-mg portion of the residue (0.99 mole) was dissolved in 1,4-dioxane (8 mL), 2-pyridone (47 mg, 0.49 mole) was added, and the solution was heated under nitrogen at 102° C. for 7 h. Additional 2-pyridone (23.5 mg, 0.25 mole) was then added and heating was continued for 4 h. At this time the solvent was removed under reduced high pressure and the residue was purified on 15 g of silica gel. Elution with 8% ethyl acetate-hexane afforded 252 mg (78%) of the thiazinone benzhydryl ester A5-D. NMR (CDCl$_3$) 7.34 (10H, m), 6.96 (1H, s), 6.48 (1H, s), 4.46 (1H, m), 3.33 (2H, s), 3.21 (1H, dd, 4, 15Hz), 2.98 (1H, dd, 9, 15Hz) .

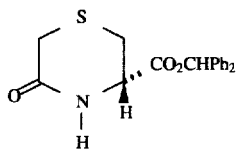

A5-D

STEP 2

The thiazinone ester A5-D (252 mg, 0.77 mole) wa disolved in dry tetrahydrofuran (5 mL) under nitrogen, and the reagent prepared from phosphoru pentaulfide and diphenyl ether according to Tetrahedron Letters 3815 (1983) (244 mg, 0.46 mole) was added. The olution was tirred for 35 min, concentrated, and the residue wa purified on silica gel (8 g). Elution with 15% ethyl acetate-hexane afforded 214 mg (81%) of the thioamide B5-D. NMR (CDCl$_3$) 8.59. (1H, s) , 7.35 (10H, m), 6.98 (1H, s), 4.39 (1H, m), 3.79 (2H, s), 3.32 (1H, dd, 4, 15Hz), 3.02 (1H, dd, 8, 15Hz).

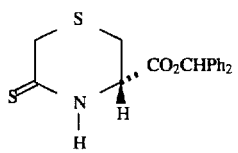

B5-D

STEP 3

The thioamide B5-D (80 mg, 0.23 mole) was dissolved with stirring in ice-cold dry tetrahydrofuran 92 mL) under nitrogen and sodium hydride (80%, 8.4 mg, 0.28 mole) was added. After 5 min stirring in an ice-bath, the reaction mixture was treeated with 30 L (0.48 mole) of methyl iodide. Reaction was complete after 25 min. Dilution with ether, followed by successive extraction with water, saturated sodium bicarbonate and saturated sodium chloride, drying and evaporation gave a product which was purified on silica gel (3 g). Elution with 10% ethyl acetate-hexane afforded 59.1 mg (75%) of the thiomethylimine C5-D. NMR (CDCl$_3$) 7.35 (10H, m), 6.96 (1H, s), 4.53 (1H, m), 3.27 (1H, dt, 5, 18Hz), 3.15 (1H, dt, 5, 18Hz), 2.99 (1H, dd, 3, 13Hz), 2.81 (1H, dd, 4, 13Hz), 2.37 (3H, s).

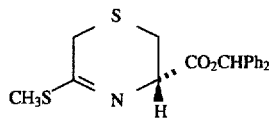

C5-D

STEP 4

The thiomethylimine C5-D (59 mg, 0.165 mole) was dissoled in tetrahydrofuran (0.5 mL) and added to a solution prepared under nitrogen from hydroxylamine hydrochloride (68.8 mg, 0.99 mole) and 1.65M methanolic sodium methylate (0.3 mL, 0.5 mole) in methanol (0.7 mL). The reaction wa complete in 10 min. The mixture was diluted with methylene chloride (10 mL), washed successively with aturated sodium bicarbonate, water and saturated sodium chloride, dried and evaporated. Chromatography on silica gel (1.5 g) and elution with 12% ethyl acetate-methylene chloride gave 52.7 mg (94%) of the oximino ester D5-D. NMR (CDCl$_3$) 7.34 (11H, m), 6.93 (1H, s), 5.97 (1H, s), 4.28 (1H, m), 3.30 (1H, d, 13Hz), 3.21 (1H, dd, 3, 13Hz), 3.16 (1H, d, 13Hz), 3.08 (1H, dd, 7, 13Hz).

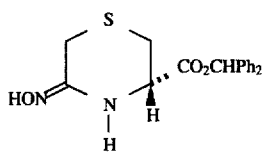

D5-D

STEP 5

The ester D5-D (47 mg) was dissolved in formic acid (1 mL). After 5 h at room temperature the reaction mixture was frozen and the solvent removed by lyophilization. The residue wa partitioned between ether and watter, the ether layer was extracted once with water, and the combined aqueous extracts were lyophilized again to yield 4-D. NMR (D$_2$O): 4.15 (1H, m), 3.50 (1H, d, 14Hz), 3.34 (1H, d, 14Hz), 3.15 (1H, dd, 6, 15Hz), 3.02 (1H, dd, 6, 15 Hz).

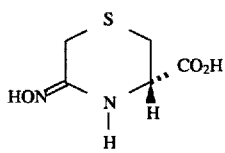

4-D

The L-enantiomer of 4 was prepared as descrikbbed above, but startin with L-cysteine in place of D-cysteine.

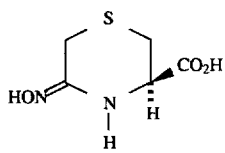

4-L

We claim:

1. A compound selected from the group consisting of compounds having antibiotic activity of the formula:

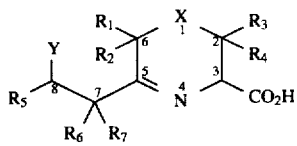

where

X=S, O, CH$_2$, or Se

Y=OH, NH$_2$, NHCOR$_9$, or SH

R$_1$,R$_2$,R$_3$,R$_4$,R$_5$,R$_6$,R$_7$ (which may be identical or different)=H, alkyl, or aryl R$_9$=a β-lactam active side chain or pharmaceutically acceptable salts thereof, wherein the β-lactam active side chain is selected from the group consisting of:

(a) a group of the formula —XO, wherein:

X=O or S, and

O=C$_{1-4}$alkyl, C$_{2-4}$alkenyl or aryl C$_{1-4}$; and, 2-carboxyvinyl, 2-methoxycarbonylvinyl, 2-ethoxycarbonylvinyl and 2-cyanovinyl or another group of the formula

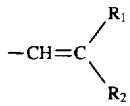

wherein R$_1$ and R$_2$ may be the same or different, and are each selected from the group consisting of hydrogen, carboxy, cyano, C$_{2-7}$, alkoxycarbonyl and substituted or unsubstituted aliphatic groups; and, (c) an unsubstituted or substituted methyl group of the formula —CH$_2$Y wherein Y is a hydrogen atom or a nucleophilic atom or nucleophilic group.

2. The compound of claim 1 wherein computer modelling indicates that the compound is capable of reacting with a serine hydroxyl group contained within a model of a penicillin-binding protein via a four-centered transition structure, wherein the model of the penicillin-binding protein comprises a model of a peptide containing the sequence Val-Gly-Ser-Val-Thr-Lys.

3. The compound of claim 2 wherein the peptide consists essentially of the sequence Ac-Val-Gly-Ser-Val-Thr-Lys-NHCH$_3$ and the dihedral angles of the peptide are approximately as follows:

| Residue | φ | ψ | ω | χ$^1$ | χ$^2$ | χ$^3$ | χ$^4$ | χ$^5$ |
|---|---|---|---|---|---|---|---|---|
| Ac |  |  | 180 |  |  |  |  |  |
| Val | −72 | 121 | 180 | −60 | 178 | 180 |  |  |
| Gly | 160 | −179 | 178 |  |  |  |  |  |
| Ser | 79 | −62 | −177 | −55 | 62 |  |  |  |
| Val | 72 | −86 | 177 | −52 | 180 | 180 |  |  |
| Thr | −71 | 152 | 176 | −172 | 176 | −179 |  |  |
| Lys | −69 | −47 | 179 | −179 | 62 | 176 | 180 | 180 |

4. The compound of claim 2 wherein computer modelling calculates that the compound has an activation energy for reaction with the serine hydroxyl group of not greater than 3 kcal/mol higher than that exhibited by a penicillin antibiotic.

5. The compound of claim 3 wherein computer modelling calculates that the compound has an activation energy for reaction with the serine hydroxyl group of not greater than 3 kcal/mol higher than that exhibited by a penicillin antibiotic.

6. The compound of claim 2 wherein computer modelling calculates that the compound has an activation energy for methanolysis of not greater than 3 kcal/mol higher than the activation energy of the corresponding reaction between methanol and N-methylazetidinone.

7. The compound of claim 3 wherein computer modelling calculates that the compound has an activation energy for methanolysis of not greater than 3 kcal/mol higher than the activation energy of the corresponding reaction between methanol and N-methylazetidinone.

8. The compound of claim 1 wherein the compound is 3-carboxy-5-(2-hydroxypropyl)-6,6-dimethyl-4-1,4-thiazine.

9. The compound of claim 8 having the S-configuration at C3.

10. The compound of claim 1 having the S-configuration at C3.

11. The compound of claim 1 wherein:

R$_1$, R$_2$, R$_3$, R$_4$, R$_6$, R$_7$=H

R$_5$=loweralkyl or aryl

Y=OH.

12. The compound of claim 11 having the S-configuration at C3.

13. The compound of claim 12 wherein R$_5$ is methyl.

14. The compound of claim 13 wherein X=S.

* * * * *

UNITED STATES PATENT AND TRADEMARK OFFICE
CERTIFICATE OF CORRECTION

PATENT NO. : 5,552,543
DATED : September 3, 1996
INVENTOR(S) : Saul Wolfe

It is certified that error appears in the above-indentified patent and that said Letters Patent is hereby corrected as shown below:

On the title page, item [75], Inventor: delete "Stephen Bruder"
the word "both" should be deleted.

Signed and Sealed this

Twelfth Day of November, 1996

Attest:

BRUCE LEHMAN

Attesting Officer          Commissioner of Patents and Trademarks